US008859284B2

(12) United States Patent
Delehanty et al.

(10) Patent No.: US 8,859,284 B2
(45) Date of Patent: Oct. 14, 2014

(54) DELIVERY OF NANOPARTICLES TO NEURONS

(71) Applicants: James B. Delehanty, Washington, DC (US); Igor L. Medintz, Springfield, VA (US); Hedi M. Mattoussi, Tallahassee, FL (US); Jeffrey R. Deschamps, Laurel, MD (US); Glyn Dawson, Chicago, IL (US); Philip E. Dawson, San Diego, CA (US); Juan Bautista Blanco-Canosa, A Coruna (ES); Kelly Boeneman, Arlington, VA (US); Kimihiro Susumu, Alexandria, VA (US); Michael H. Stewart, Springfield, VA (US); Ryan Walters, Chicago, IL (US)

(72) Inventors: James B. Delehanty, Washington, DC (US); Igor L. Medintz, Springfield, VA (US); Hedi M. Mattoussi, Tallahassee, FL (US); Jeffrey R. Deschamps, Laurel, MD (US); Glyn Dawson, Chicago, IL (US); Philip E. Dawson, San Diego, CA (US); Juan Bautista Blanco-Canosa, A Coruna (ES); Kelly Boeneman, Arlington, VA (US); Kimihiro Susumu, Alexandria, VA (US); Michael H. Stewart, Springfield, VA (US); Ryan Walters, Chicago, IL (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/679,335

(22) Filed: Nov. 16, 2012

(65) Prior Publication Data
US 2013/0129627 A1    May 23, 2013

Related U.S. Application Data

(63) Continuation-in-part of application No. 12/908,601, filed on Oct. 20, 2010, now Pat. No. 8,409,858, and a continuation-in-part of application No. 13/209,974, filed on Aug. 15, 2011, now Pat. No. 8,512,755.

(60) Provisional application No. 61/253,921, filed on Oct. 22, 2009.

(51) Int. Cl.
| | |
|---|---|
| *C12N 5/00* | (2006.01) |
| *A61K 38/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |
| *A61K 47/20* | (2006.01) |
| *C12Q 1/02* | (2006.01) |
| *B82Y 5/00* | (2011.01) |
| *A61K 47/48* | (2006.01) |
| *A61K 49/00* | (2006.01) |
| *G01N 33/50* | (2006.01) |

(52) U.S. Cl.
CPC . *A61K 47/20* (2013.01); *C12Q 1/02* (2013.01); *B82Y 5/00* (2013.01); *A61K 47/48192* (2013.01); *A61K 47/48238* (2013.01); *A61K 47/48861* (2013.01); *A61K 47/48884* (2013.01); *A61K 49/0067* (2013.01); *G01N 33/5058* (2013.01); *A61K 47/4823* (2013.01)
USPC .......................................... 435/375; 530/300

(58) Field of Classification Search
CPC ................... A61K 47/4823; A61K 47/48238; A61K 47/48861; A61K 47/48884; A61K 49/0067; A61K 47/20; A61K 47/48192; B82Y 5/00; C12Q 1/02
See application file for complete search history.

(56) References Cited

U.S. PATENT DOCUMENTS

| 8,409,858 B2 * | 4/2013 | Delehanty et al. ............ 435/375 |
| 8,512,755 B2 * | 8/2013 | Medintz et al. ............... 424/489 |
| 2011/0097797 A1 * | 4/2011 | Delehanty et al. ............ 435/375 |
| 2013/0130296 A1 * | 5/2013 | Delehanty et al. .............. 435/29 |
| 2013/0158244 A1 * | 6/2013 | Delehanty et al. ........... 536/23.1 |

OTHER PUBLICATIONS

Pathak et al. Quantum Dot Applications to Neuroscience: New Tools for Probin Neurons and Glia. The Journal of Neuroscience, Feb. 15, 2006, vol. 26, No. 7, pp. 1893-1895.*
Delehanty et al. Delivering quantum dot-peptide bioconjugates to the cellular cytosol: escaping from the endolysosomal system. Integr. Biol. 2010, First publisheld on the web May 4, 2010, vol. 2, pp. 265-277.*

* cited by examiner

*Primary Examiner* — Marcela M Cordero Garcia
(74) *Attorney, Agent, or Firm* — US Naval Research Laboratory; Roy Roberts

(57) ABSTRACT

A peptide attached to a nanoparticles (such as quantum dots) selectively directs the nanoparticles to neurons in a tissue or organism.

13 Claims, 19 Drawing Sheets

SEQUENCE LISTING

```
<160> NUMBER OF SEQ ID NOS: 42

<210> SEQ ID NO 1
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (14)..(14)
<223> OTHER INFORMATION: alpha-amino isobutyric acid

<400> SEQUENCE: 1
```

```
Arg Arg Arg Arg Arg Arg Arg Arg Arg Gly Gly Leu Ala Xaa Ser Gly
1               5                   10                  15

Trp Lys His His His His His His
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: alpha-amino isobutyric acid

<400> SEQUENCE: 2

His His His His His His Trp Gly Leu Ala Xaa Ser Gly Pro Lys Lys
1               5                   10                  15

Lys Arg Lys Val
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl

<400> SEQUENCE: 3

Trp Gly Xaa Val Lys Ile Lys Lys Pro Pro Pro Pro Pro Pro Pro Pro
1               5                   10                  15

Pro Gly Gly His His His His His His
            20                  25

<210> SEQ ID NO 4
<211> LENGTH: 24
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: (1)..(1)
<223> OTHER INFORMATION: N-acetylglycine
<220> FEATURE:
<221> NAME/KEY: LIPID
<222> LOCATION: (2)..(2)
<223> OTHER INFORMATION: palmitoyldiamoniproprionyl

<400> SEQUENCE: 4

Gly Xaa Val Lys Ile Lys Lys Pro Pro Pro Pro Pro Pro Pro Pro Pro
1               5                   10                  15

Gly Gly His His His His His His
            20

<210> SEQ ID NO 5
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
```

```
<222> LOCATION: (1)..(1)
<223> OTHER INFORMATION: N-acetylglycine
<220> FEATURE:
<221> NAME/KEY: LIPID
<222> LOCATION: (2)..(2)
<223> OTHER INFORMATION: palmitoyldiamoniproprionyl

<400> SEQUENCE: 5

Gly Xaa Val Lys Ile Lys Lys Gly Leu Ala Ala Ala Ala Gly Gly His
1               5                   10                  15

His His His His His
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: ACETYLATION
<222> LOCATION: (1)..(1)
<223> OTHER INFORMATION: N-acetylglycine
<220> FEATURE:
<221> NAME/KEY: LIPID
<222> LOCATION: (2)..(2)
<223> OTHER INFORMATION: palmitoyldiamoniproprionyl

<400> SEQUENCE: 6

Gly Xaa Val Lys Ile Lys Lys Gly Leu Ala Pro Ala Ala Gly Gly His
1               5                   10                  15

His His His His His
            20

<210> SEQ ID NO 7
<211> LENGTH: 5
<212> TYPE: PRT
<213> ORGANISM: Artificial Sequence
<220> FEATURE:
<223> OTHER INFORMATION: Synthetic construct

<400> SEQUENCE: 7

Val Lys Ile Lys Lys
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic construct

<400> SEQUENCE: 8

His His His His His His Ser Leu Gly Ala Ala Ala Gly Ser Gly Cys
1               5                   10                  15

<210> SEQ ID NO 9
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl

<400> SEQUENCE: 9
```

```
Trp Gly Xaa Val Lys Ile Lys Lys Gly Leu Ala Ala Ala Ala Gly Gly
1               5                   10                  15

His His His His His His
            20

<210> SEQ ID NO 10
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamonipropionyl

<400> SEQUENCE: 10

Trp Gly Xaa Val Lys Ile Lys Lys Gly Leu Ala Pro Ala Ala Gly Gly
1               5                   10                  15

His His His His His His
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamonipropionyl

<400> SEQUENCE: 11

Trp Gly Xaa Val Lys Ile Lys Lys Pro Pro Pro Pro Gly Gly His His
1               5                   10                  15

His His His His
            20

<210> SEQ ID NO 12
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (9)..(17)
<223> OTHER INFORMATION: Aib

<400> SEQUENCE: 12

Trp Gly Xaa Val Lys Ile Lys Lys Xaa Xaa Xaa Xaa Xaa Xaa Xaa Xaa
1               5                   10                  15

Xaa Gly Gly His His His His His His
            20                  25

<210> SEQ ID NO 13
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
```

```
<222> LOCATION: (3)..(3)
<223> OTHER INFORMATION: palmitoyldiamoniproprionyl

<400> SEQUENCE: 13

Trp Gly Xaa Val Lys Ile Lys Lys Pro Pro Pro Pro Pro Pro Pro
1               5                   10                  15

Pro Pro Pro Pro Gly Gly His His His His His His
            20                  25

<210> SEQ ID NO 14
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl

<400> SEQUENCE: 14

Trp Gly Xaa Val Lys Ile Lys Lys Pro Pro Pro Pro Pro Pro Pro
1               5                   10                  15

Pro Pro Pro Pro Pro Pro Pro Gly Gly His His His His His His
            20                  25                  30

<210> SEQ ID NO 15
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl

<400> SEQUENCE: 15

Trp Gly Xaa Pro Pro Pro Pro Pro Pro Pro Pro Gly Gly His His
1               5                   10                  15

His His His His
            20

<210> SEQ ID NO 16
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl

<400> SEQUENCE: 16

Trp Gly Xaa Val Arg Arg Arg Ile Arg Arg Pro Pro Pro Pro Pro
1               5                   10                  15

Pro Pro Pro Gly Gly His His His His His His
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MISC_FEATURE
<222> LOCATION: (3)..(3)
<223> OTHER INFORMATION: Dpr (2,3-Diaminopropionic acid)

<400> SEQUENCE: 17

Trp Gly Xaa Val Arg Arg Ile Arg Arg Pro Pro Pro Pro Pro
1               5                   10                  15

Pro Pro Pro Gly Gly His His His His His
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniprionyl
<220> FEATURE:
<221> NAME/KEY: MISC_FEATURE
<222> LOCATION: (13)..(13)
<223> OTHER INFORMATION: Aib

<400> SEQUENCE: 18

Trp Gly Xaa Ala Gly Ala Gly Gly Ala Ala Ala Ala Xaa Ala Ala Ala
1               5                   10                  15

Ala Gly Gly His His His His His
            20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniprionyl

<400> SEQUENCE: 19

Trp Gly Xaa Val Arg Leu Pro Pro Pro Val Arg Leu Pro Pro Pro Val
1               5                   10                  15

Arg Leu Pro Pro Pro Gly Gly His His His His His His
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Dpr (2,3-Diaminopropionic acid)

<400> SEQUENCE: 20

Trp Gly Xaa Val Arg Leu Pro Pro Pro Val Arg Leu Pro Pro Pro Val
1               5                   10                  15

Arg Leu Pro Pro Pro Gly Gly His His His His His His
            20                  25

<210> SEQ ID NO 21
<211> LENGTH: 25
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Dpr (2,3-Diaminopropionic acid)

<400> SEQUENCE: 21

Trp Gly Xaa Val Lys Ile Lys Lys Pro Pro Pro Pro Pro Pro Pro
1               5                   10                  15

Pro Gly Gly His His His His His His
            20                  25

<210> SEQ ID NO 22
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl
<220> FEATURE:
<221> NAME/KEY: LIPID
<222> LOCATION: (5)..(5)
<223> OTHER INFORMATION: palmitoyldiamoniproprionyl

<400> SEQUENCE: 22

Trp Gly Xaa Gly Xaa Val Lys Ile Lys Lys Pro Pro Pro Pro Pro
1               5                   10                  15

Pro Pro Pro Gly Gly His His His His His His
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: dipalmitoyldiamoniproprionyl

<400> SEQUENCE: 23

Trp Gly Xaa Val Lys Ile Lys Lys Pro Pro Pro Pro Pro Pro Pro
1               5                   10                  15

Pro Gly Gly His His His His His His
            20                  25

<210> SEQ ID NO 24
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: a hydrolyzable form of palmitate

<400> SEQUENCE: 24

Trp Gly Xaa Val Cys Ile Lys Lys Pro Pro Pro Pro Pro Pro Pro
1               5                   10                  15

Pro Gly Gly His His His His His His
```

-continued

```
                 20                  25

<210> SEQ ID NO 25
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: diaminobutyrate

<400> SEQUENCE: 25

Trp Gly Xaa Val Lys Ile Lys Lys Pro Pro Pro Pro Pro Pro Pro
1               5                   10                  15

Pro Gly Gly His His His His His His
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: octanoyl modified diaminopropionic acid

<400> SEQUENCE: 26

Trp Gly Xaa Val Lys Ile Lys Lys Pro Pro Pro Pro Pro Pro Pro
1               5                   10                  15

Pro Gly Gly His His His His His His
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: octanoyl modified tryptophan
<220> FEATURE:
<221> NAME/KEY: MISC_FEATURE
<222> LOCATION: (3)..(3)
<223> OTHER INFORMATION: octanoyl modified diaminopropionic acid

<400> SEQUENCE: 27

Xaa Gly Xaa Val Lys Ile Lys Lys Pro Pro Pro Pro Pro Pro Pro
1               5                   10                  15

Pro Gly Gly His His His His His His
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: perfluro-modified diaminopropionic acid

<400> SEQUENCE: 28
```

```
Trp Gly Xaa Val Lys Ile Lys Lys Pro Pro Pro Pro Pro Pro Pro
1               5                   10                  15

Pro Gly Gly His His His His His His
            20                  25

<210> SEQ ID NO 29
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: cholesterol-modified diaminopropionic acid

<400> SEQUENCE: 29

Trp Gly Xaa Val Lys Ile Lys Lys Pro Pro Pro Pro Pro Pro Pro
1               5                   10                  15

Pro Gly Gly His His His His His His
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: modified with cholesterol

<400> SEQUENCE: 30

Trp Gly Cys Val Lys Ile Lys Lys Pro Pro Pro Pro Pro Pro Pro
1               5                   10                  15

Pro Gly Gly His His His His His His
            20                  25

<210> SEQ ID NO 31
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: FARNESYL

<400> SEQUENCE: 31

Trp Gly Cys Val Lys Ile Lys Lys Pro Pro Pro Pro Pro Pro Pro
1               5                   10                  15

Pro Gly Gly His His His His His His
            20                  25

<210> SEQ ID NO 32
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (20)..(20)
<223> OTHER INFORMATION: palmitoyldiamonipropionyl
```

```
<400> SEQUENCE: 32

His His His His His His Gly Gly Pro Pro Pro Pro Pro Pro Pro
1               5                   10                  15

Pro Trp Gly Xaa Val Lys Ile Lys Lys
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: LIPID
<222> LOCATION: (25)..(25)
<223> OTHER INFORMATION: palmitoyldiamoniproprionyl

<400> SEQUENCE: 33

His His His His His His Gly Gly Pro Pro Pro Pro Pro Pro Pro
1               5                   10                  15

Pro Val Lys Ile Lys Lys Xaa Gly Trp
            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (8)..(8)
<223> OTHER INFORMATION: palmitoyldiamoniproprionyl

<400> SEQUENCE: 34

Val Lys Ile Lys Lys Trp Gly Xaa Pro Pro Pro Pro Pro Pro Pro
1               5                   10                  15

Pro Gly Gly His His His His His His
            20                  25

<210> SEQ ID NO 35
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: LIPID
<222> LOCATION: (3)..(3)
<223> OTHER INFORMATION: palmitoyldiamoniproprionyl

<400> SEQUENCE: 35

Trp Gly Xaa Ala Arg Arg Arg Ile Arg Arg Pro Pro Pro Pro Pro
1               5                   10                  15

Pro Pro Pro Gly Gly Lys
            20

<210> SEQ ID NO 36
<211> LENGTH: 19
<212> TYPE: PRT
<213> ORGANISM: Artificial Sequence
<220> FEATURE:
<223> OTHER INFORMATION: Synthetic construct
```

```
<220> FEATURE:
<221> NAME/KEY: LIPID
<222> LOCATION: (3)..(3)
<223> OTHER INFORMATION: palmitoyldiamonipropionyl
<220> FEATURE:
<221> NAME/KEY: MISC_FEATURE
<222> LOCATION: (19)..(19)
<223> OTHER INFORMATION: dye-labeled

<400> SEQUENCE: 36

Trp Gly Xaa Val Lys Ile Lys Lys Pro Pro Pro Pro Pro Pro Pro
1               5                   10                  15

Gly Gly Lys

<210> SEQ ID NO 37
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: dye-labeled
<220> FEATURE:
<221> NAME/KEY: LIPID
<222> LOCATION: (5)..(5)
<223> OTHER INFORMATION: palmitoyldiamonipropionyl

<400> SEQUENCE: 37

Lys Trp Gly Ser Xaa Ala Ala Ala Leu Gly Gly Arg Arg Arg Arg
1               5                   10                  15

Arg Arg Arg Arg Arg
                20

<210> SEQ ID NO 38
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (24)..(24)
<223> OTHER INFORMATION: Aib

<400> SEQUENCE: 38

Lys Glu Thr Trp Trp Glu Thr Trp Trp Thr Glu Trp Ser Gln Pro Lys
1               5                   10                  15

Lys Lys Arg Lys Val Ser Gly Xaa Ala Ala Ala Gly Gly His His His
                20                  25                  30

His His His
        35

<210> SEQ ID NO 39
<211> LENGTH: 18
<212> TYPE: PRT
<213> ORGANISM: Artificial Sequence
<220> FEATURE:
<223> OTHER INFORMATION: Synthetic construct

<400> SEQUENCE: 39

Cys Pro Pro Pro Pro Pro Pro Pro Pro Gly Gly His His His His
1               5                   10                  15

His His
```

-continued

```
<210> SEQ ID NO 40
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (15)..(15)
<223> OTHER INFORMATION: Aib

<400> SEQUENCE: 40

Arg Arg Arg Arg Arg Arg Arg Arg Arg Gly Gly Leu Ala Ala Xaa Ser
1               5                   10                  15

Gly Trp Lys His His His His His His
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: modified with tetramethylrhodamine
<220> FEATURE:
<221> NAME/KEY: MISC_FEATURE
<222> LOCATION: (3)..(3)
<223> OTHER INFORMATION: palmitoyldiamoniproprionyl

<400> SEQUENCE: 41

Lys Gly Xaa Val Lys Ile Lys Lys Pro Pro Pro Pro Pro Pro Pro Pro
1               5                   10                  15

Pro Gly Gly His His His His His His
            20                  25

<210> SEQ ID NO 42
<211> LENGTH: 4
<212> TYPE: PRT
<213> ORGANISM: Artificial Sequence
<220> FEATURE:
<223> OTHER INFORMATION: synthetic construct

<400> SEQUENCE: 42

Lys Ile Lys Lys
1
```

DELIVERY OF NANOPARTICLES TO NEURONS

CROSS-REFERENCE TO RELATED APPLICATIONS

This application is a Continuation-in-Part of U.S. patent application Ser. No. 12/908,601 filed on Oct. 20, 2010, which claims the benefit of U.S. Provisional Patent Application No. 61/253,921 filed on Oct. 22, 2009, each of which is incorporated herein by reference.

This application is also a Continuation-in-Part of U.S. patent application Ser. No. 13/209,974 filed on Aug. 15, 2011, incorporated herein by reference.

This application is further related to U.S. patent application Ser. No. 12/606,766 filed on Oct. 27, 2009, incorporated herein by reference.

BACKGROUND

Quantum dots (QDs) provide many advantageous features that include high quantum yield, broad absorption spectra, large achievable Stokes shifts, narrow symmetric, size tunable emission spectra, and exceptional resistance to photo- and chemical degradation, making them attractive reagents for the long-term visualization of cellular structures and processes. See references 1-4.

The methods employed to date for the intracellular delivery of QDs or other nanoparticles (NPs) can be grouped into three generalized categories based on their physicochemical nature. Passive delivery is a nonspecific process that relies on the inherent physicochemical properties of the QD (surface charge and/or functionalization) to mediate uptake. Facilitated delivery utilizes a delivery agent (e.g., a cationic peptide or a polymer) that is covalently attached to or electrostatically complexed with the QDs to specifically induce internalization. Both these techniques, while noninvasive, typically utilize the endocytic pathway which results in encapsulation of the QDs within intracellular endolysosomal vesicles and thus requires further strategies to liberate the sequestered QDs to the cytosol if that is ultimately desired. Examples methods of facilitated delivery include using additional chemicals such as sucrose or chloroquine or adding polymers such as polyethyleneimine during delivery to disrupt the endosomes by osmotic shock: such methods are generally quite toxic. Lastly, active delivery methods such as electroporation and microinjection deliver QDs directly to the cytosol through physical manipulation of the cell. However, these are highly invasive techniques that can often compromise the integrity of cellular structures and substantially reduce cellular viability (see reference 10). Thus, each of the previously described methods for delivery of nanoparticles (including quantum dots) is deficient in some way.

Described herein are improvements in delivery of nanoparticles.

BRIEF SUMMARY

In one embodiment, a peptide for delivery of a nanoparticle to the cytosol comprises: (a) a nanoparticle association domain; (b) a spacer domain; (c) an uptake domain; and (d) a vesicle escape domain comprising a non-hydrolyzable lipid moiety, wherein the spacer domain is between the nanoparticle association domain and the uptake and vesicle escape domains, and wherein the peptide, when attached to an extracellular nanoparticle, is effective to induce uptake of the nanoparticle by a cell and delivery of the nanoparticle to the cytosol of the cell.

In a further embodiment, the spacer comprises from between 6 and 15 proline residues, for example 6, 7, 8, 9, 10, 11, 12, 13, 14, or 15 proline residues.

In another embodiment, a nanoparticle is delivered to the cytosol of a cell by providing to a cell with a nanoparticle attached to such a peptide.

In an additional embodiment, a method of delivery to a neuron in a tissue includes providing to the tissue a nanoparticle bound to a compound of the formula:

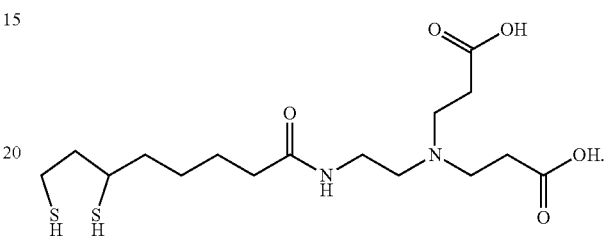

In a yet further embodiment, a method of delivery to a neuron in a tissue includes providing to the tissue a nanoparticle bound to:
(1) a peptide comprising
   (a) a nanoparticle association domain comprising polyhistidine;
   (b) a spacer domain comprising 8, 9, or 10 proline residues;
   (c) an uptake domain comprising SEQ ID No: 7; and
   (d) a vesicle escape domain comprising a non-hydrolyzable palmitic acid,
wherein the spacer domain is between the nanoparticle association domain and the uptake and vesicle escape domains, and

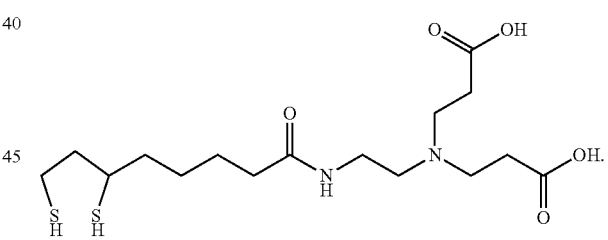

(2) a compound of the formula:
Exemplary nanoparticles include quantum dots.

BRIEF DESCRIPTION OF THE DRAWINGS

FIG. 1A shows normalized absorbance and emission of 510, 550 nm QDs and AlexaFluor 647 (AF647). FIG. 1B shows schematics of various QD conjugates.

FIG. 2 shows QD-CPP internalization and colocalization over time. Cells were washed, fixed and stained with DAPI in FIG. 2A or supplied with fresh media and cultured for 4, 24 or 72 h prior to fixation and DAPI-staining in FIG. 2B. In FIG. 2A the DAPI, QD and marker signals are shown individually and merged while in FIG. 2B only the merged images are shown. Arrows indicate areas of colocalization. The scale bar is 10 μm.

FIG. 3B shows merged images of DAPI-stained nuclei, QD and Cy3 signals at 1, 4, 24 and 72 h after conjugate delivery, where the scale bar is 10 µm. FIG. 3C shows the calculated Cy3/QD emission ratio is shown plotted as a function of time after initial conjugate delivery. FIG. 3D shows observed fluorescence for transferrin-Cy3 conjugates delivered alone (no QDs) is plotted as a function of time. In FIGS. 3C and 3D the data points were fitted with a dose response logistic curve fit function.

In FIG. 4C 510 nm DHLA-PEG QDs (800 nM) were delivered using the pinocytic reagent, Influx™. 520 nm QDs (75 nM) capped with a 1:1 mixed surface of DHLA:DHLA-PEG were delivered to HEK 293T/17 cells using Lipofectamine2000™ in FIG. 4D or the branched polymer, polyethyleneimine in FIG. 4E. The images in FIGS. 4D and 4E show merged images of the QD signal and the fluorescence from the endocytic marker, AlexaFuor647-transferrin. In FIGS. 4A through E the cells were imaged after fixation and staining with DAPI. In FIG. 4F 550 nm DHLA-PEG QDs (100 nM) appended with 25 CPP were coincubated with 100 µM pyrenebutyrate in PBS for 30 min at 37° C. prior to washing and imaging of live cells (no DAPI present). The scale bar is 10 µm.

FIGS. 6C and 6D show corresponding cytotoxicity data for the inhibition of cellular proliferation by QD-Palm-1 complexes in COS-1 and HEK 293T/17 cells, respectively. Cells were incubated with the materials for 1 h, washed, and subsequently cultured for 72 h prior to viability assay. When the QDs are present, the concentration given is that of the QDs. Each data point represents the mean±SD of triplicate measurements.

FIG. 7A shows a general schematic of an exemplary NP-peptide assembly. The schematic peptide shown consists of multiple functional domains: a NP association domain (1); a spacer domain (2); and multiple domains that impart biological activity (3 and 4). FIG. 7B shows a QD-peptide assembly for intracellular uptake and endosomal escape. The modular peptide consists of a hexa-histidine (H6) domain for assembly to the QD surface, a proline-rich spacer domain (P9GG), a positively charged lysine-rich domain (VKIKK, SEQ ID No: 7) for cellular association and uptake, and a synthetic palmitic acid group ((Pal)Dap) for cell membrane association and insertion and vesicle escape.

In FIG. 9A the assembles have Palm-1b, in FIG. 9B Palm-2b, and in FIG. 9C Palm-3b.

FIG. 11A shows the structure of CL4 (above) shown in relation to a PEG ligand (below). FIG. 11B is a schematic of Palm1 peptide conjugated to a QD via histidine binding to the ZnS surface.

FIGS. 12A-12D are representative images of cell bodies located in the CA3 cell layer of the rat hippocampus. QDs (red) containing the CL4 coat were conjugated to Palm1 and applied to the hippocampal slice culture preparation for 24 h. Cells were fixed and imaged with confocal microscopy (Nissl is green, Dapi is blue). The QDs showed neuronal targeting and intracellular localization, exhibiting a punctate, perinuclear distribution. Scale bars in FIGS. 12A and B are 20 µm and in FIGS. 12C and D are 10 µm.

FIGS. 14C-F employ Sytox staining No QD-induced cytotoxicity was observed in the neurons after 72 h in culture. FIG. 14C employs NeuN stain showing cytoarchitecture. FIG. 14D is a negative control. FIG. 14E shows CL4 QD-Palm1 after 72 h. FIG. 14F is a positive control. Scale bars in FIGS. 14A and B are 20 µm and in FIG. 14C, 200 um.

FIG. 15A displays CL4 coated QDs showing intracellular delivery to neuronal cell bodies in the CA3 cell layer of a hippocampal slice culture after 24 h application. FIG. 15B shows that PEG coated QDs were not delivered intracellularly and remained on the periphery of cell bodies in the CA3 cell layer after 24 h. FIG. 15C is the same image as FIG. 15A, showing the cell bodies. FIG. 15D is the same image as FIG. 15B, showing the QD distribution surrounding the cell bodies. QD is red, Nissl is green, DAPI is blue. Scale bars are 20 µm FIG. 16A is a representative z-stack confocal image (representing around 30 separate images stacked together) of QD-peptide distribution within a portion of a slice. This confirms that the application method results in distribution past the surface of our slice preparations. FIGS. 16B and C are re-sliced z-stacks of several neurons showing intracellular distribution of QDs within single neurons. Yellow bar indicates site of re-slicing with the re-sliced z-plane is below. QDs are red, Nissl is green, DAPI is blue. Scale bars A,B are 10 µm, C is 20 µm.

FIG. 17A shows pyramidal neuron off of the CA3 cell layer showing diffuse distribution of QD-peptide after 24 h. FIG. 17B is the same neuron as in FIG. 17A at higher magnification, with the inset showing Nissl and DAPI stains of same image (QDs are red, Nissl is green, DAPI is blue). FIG. 17C shows a pyramidal neuron adjacent to the CA3 cell layer showing diffuse distribution of QD-peptide well into the processes after 24 h. FIG. 17D is the same neuron as in FIG. 17C at higher magnification. Scale bars are 20 µm in FIGS. 17A and C, and 10 µm in FIGS. 17B and D.

FIGS. 18A-C show that CL4 QD conjugated to the Palm1 peptide is delivered intracellularly and largely dispersed throughout the cytosol (Black dots). FIGS. 18D and E show CL4 QD without peptide is delivered to the cell but largely remains sequestered around intracellular organelles. FIG. 18F is a negative control. Arrows point to QDs. Scale bars are 200 nm.

DETAILED DESCRIPTION

Figure 1A:
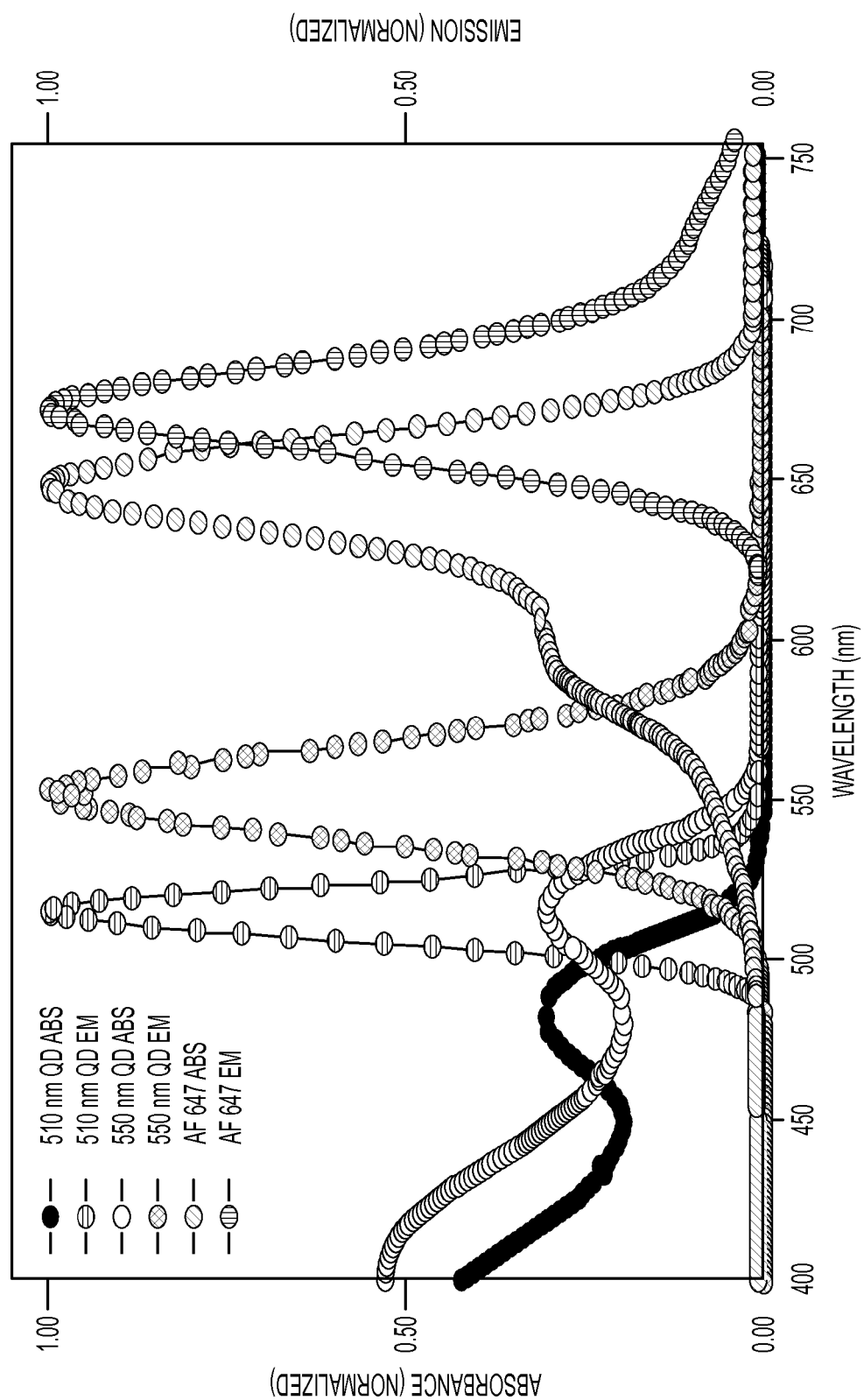
FIGS. 1A and 1B show spectral properties and schematic of QD conjugates examined herein.

This invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention. For instance, although several examples use quantum dots, one of ordinary in the art would understand that similar techniques can be used with other nanoparticles as described below.

All publications mentioned herein are hereby incorporated by reference for the purpose of disclosing and describing the particular materials and methodologies for which the reference was cited.

Use of the singular forms "a," "an," and "the" include plural references unless the context clearly dictates otherwise. Thus, for example, reference to "a nanoparticle" includes a plurality of such nanoparticles.

Terms such as "connected," "attached," "linked," and "conjugated" are used interchangeably herein and encompass direct as well as indirect connection, attachment, linkage or conjugation unless the context clearly dictates otherwise.

Where a range of values is recited, it is to be understood that each intervening integer value, and each fraction thereof, between the recited upper and lower limits of that range is also specifically disclosed, along with each sub-range between such values. The upper and lower limits of any range can independently be included in or excluded from the range, and each range where either, neither or both limits are included is also encompassed. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

"Polypeptide" and "protein" are used interchangeably herein and include a molecular chain of amino acids linked through peptide bonds. The terms do not refer to a specific length of the product. Thus, "peptides," "oligopeptides," and "proteins" are included within the definition of polypeptide. The terms include polypeptides containing post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide. The peptides that can be used as described herein include multiple amino acids, which may be natural, synthetic or a mixture thereof. Each peptide may express different side chains, if desired. Other amide oligomers such as beta peptides, peptoids and peptide nucleic acids may also be used.

The term "proline-rich spacer" as used herein refers to a spacer comprising at least about 50% proline residues, optional at least 60%, 70%, 80%, or 90% proline residues, or optionally entirely proline residues. Preferably, the spacer has a length of from six to eighteen residues.

The term "non-hydrolyzable" as used herein refers to a moiety that remains substantially not hydrolyzed by the normal action of intracellular enzymes, so that it remains attached to a peptide. As described in more detail below, it is believed that the property of being non-hydrolyzable contributes to escape from the endosomal system into the cytosol.

The terms "semiconductor nanocrystal," "SCNC," "SCNC nanocrystal," "quantum dot," and "QD" are used interchangeably herein and refer to an inorganic crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their uniform nanometer size.

A QD is capable of emitting electromagnetic radiation upon excitation (i.e., the QD is luminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate.

The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbSe, and an alloy or a mixture thereof. Preferred shell materials include ZnS.

A QD is optionally surrounded by a "coat" of an organic capping agent. The organic capping agent may be any number of materials, but has an affinity for the QD surface. In general, the capping agent can be an isolated organic molecule, a polymer (or a monomer for a polymerization reaction), an inorganic complex, or an extended crystalline structure. The coat can be used to convey solubility, e.g., the ability to disperse a coated QD homogeneously into a chosen solvent, functionality, binding properties, or the like. In addition, the coat can be used to tailor the optical properties of the QD.

Thus, the quantum dots herein include a coated core, as well as a core/shell QD.

The term "nanoparticle" as used herein includes the above-mentioned QDs in addition to other nano-scale and smaller particles such as carbon nanotubes, proteins, polymers, dendrimers, viruses, and drugs. A nanoparticle has a size of less than about 1 micron, optionally less than about 900, 800, 700, 600, 500, 400, 300, 100, 80, 60, 50, 40, 30, 20, 10, 9, 8, 7, 6, 5, 4, 3, 2, or 1 nanometers. A nanoparticle may have various shapes such as a rod, a tube, a sphere, and the like. Nanoparticles may be made from various materials including metals, carbon (such as carbon nanotubes), polymers, and combinations thereof. A nanoparticle for cytosolic delivery by a peptide may be referred to as a cargo or payload.

The QDs as well as other nanoparticles, may be biofunctionalized for use in, for example, in vivo tissue and cellular labeling, development of biological labels based on quantum dot probes and biosensor development. Other uses of the biofunctionalized materials may include protein ordering for molecular electronics where quantum dots could serve as fluorophores and electronic components, energy harvesting, quantum dot based bar coding, and drug discovery assays where the fluorescence properties of the quantum dots may be combined with bioactive peptides.

The functionalization may be used to impart a variety of properties to quantum dots and/or nanoparticles including, but not limited to, the ability to homogeneously disperse the quantum dots and/or nanoparticles in buffer solutions and a variety of polar solvents at various pH values; biocompatibility; biotargeting by allowing the use of peptide-driven binding to specific cell receptors such as the TAT sequence; providing specific points of modification directly on the quantum dot substrate by using, for example, amine groups for reacting with N-hydroxysuccinimide esters; providing bio-recognized sequences such as the AviTag sequence which is specifically biotinylated as an example; providing protease-recognized cleavage sites; providing polyhistidines for metal affinity coordination; and providing functional groups for further targeted modification, including, for example, amino groups, carboxyl groups, azide groups, alkyne groups, hydrazine groups, aldehyde groups, aminooxy groups, ketone groups, maleimide groups or thiol groups for dye/quencher or other chemical modification steps.

Materials.

Sucrose, chloroquine, and polyethyleneimine (PEI, 25 kDa Mw, branched polymer) were purchased from Sigma (St. Louis, Mo.). Influx™ reagent, Lipofectamine2000™ and the subcellular organelle markers AlexaFluor 647-transferrin ($\lambda$abs 650 nm/$\lambda$em 668 nm), BODIPY TR-ceramide-BSA ($\lambda$abs 589 nm/$\lambda$em 616 nm), LysoTracker Red DND-99 ($\lambda$abs 577 nm/$\lambda$em 590 nm) and the nuclear stain DAPI ($\lambda$abs 350 nm/$\lambda$em 450 nm) were obtained from Invitrogen (Carlsbad, Calif.). PULSin™ was purchased from Polyplus-transfection (New York, N.Y.). Other materials were obtained as described.

Quantum Dots.

CdSe—ZnS core-shell QDs with emission maxima centered at 510, 520, or 550 nm were synthesized and made hydrophilic by exchanging the native trioctylphosphine/trioctylphosphine oxide (TOP/TOPO) capping shell with either DHLA (dihydrolipoic acid) or polyethylene glycol (PEG) appended DHLA ligands as described previously (see references 17 and 18). These are subsequently referred to herein as DHLA or DHLA-PEG ligands. In general, PEGylated-QDs are preferred as they provide superior intracellular solubility and pH stability; however, some of the delivery reagents utilized required QDs with charged surfaces to mediate electrostatic interactions. 510 nm QDs capped with either DHLA or DHLA-PEG ligands were used for CPP-mediated delivery. The 520 nm QDs delivered by PULSin™, PEI or Lipofectamine2000™ were capped with a 1:1 ratiometric mix of DHLA and DHLA-PEG ligands. 550 nm QDs used for electroporation, nucleofection, Influx™- and peptide-mediated delivery were capped with DHLA-PEG.

Figure 1B:
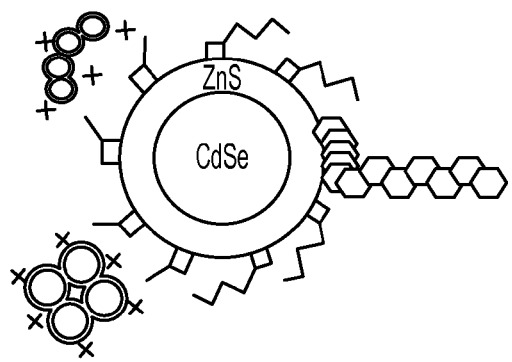
Figure 1B:
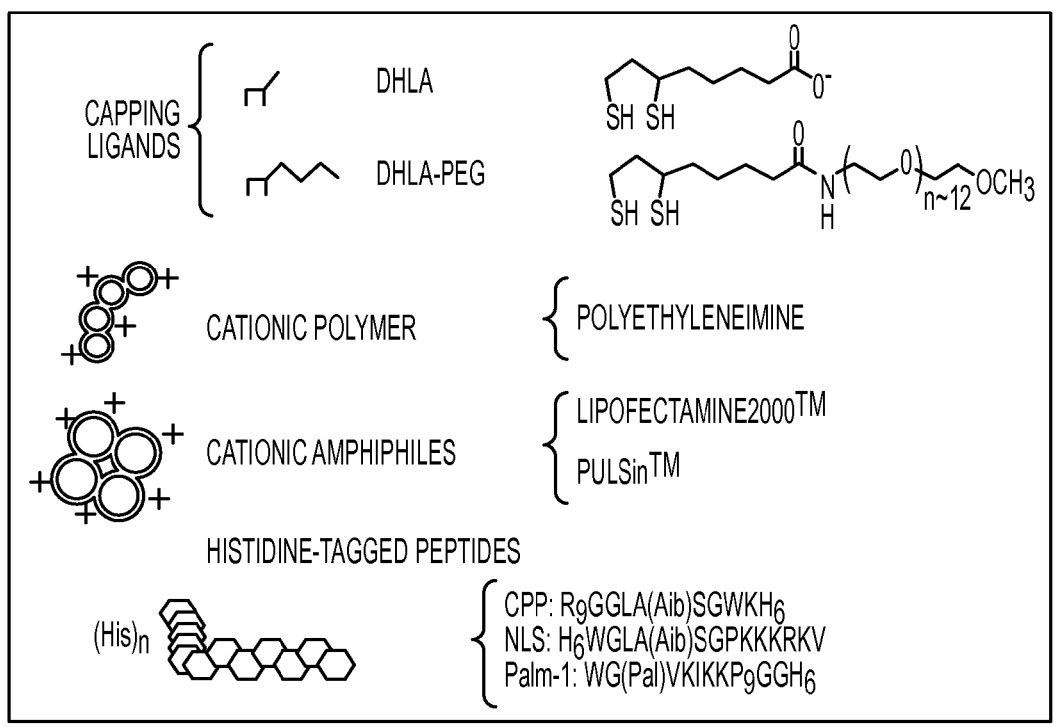

FIG. 1A shows normalized absorbance and emission of 510, 550 nm QDs and AlexaFluor 647 (AF647). FIG. 1B is a schematic of QD conjugates for facilitated QD delivery. CdSe—ZnS core-shell QDs capped with either charged DHLA or neutral DHLA-PEG ligands are noncovalently associated with linear cationic polymers, cationic liposomes or histidine-tagged peptides to mediate QD endocytosis. The sequences of the CPP, NLS, and Palm-1 peptides used herein are also shown. In FIG. 1, "Aib" refers to alpha-amino isobutyric acid and "Pal" refers to a nonhydrolyzable palmitate group that is covalently attached to a diaminopropionic acid functionality synthesized into the peptide backbone.

Peptides.

The cell-penetrating peptide (CPP) having the sequence R9GGLA(Aib)SGWKH6 (SEQ ID No: 1) was used. "Aib" represents the artificial residue alpha-amino isobutyric acid. The polyarginine tract (R9) mediates cellular uptake and is separated from a polyhistidine tract (H6) for assembly to the QD surface by a linker domain (GGLA(Aib)SGWK). The nuclear localization signal (NLS) containing peptide was synthesized with the sequence H6WGLA(Aib)SGP-KKKRKV(SEQ ID No: 2). The palmitoylated peptide (Palm-1) sequence was WG(Pal)VKIKKP9GGH6 (SEQ ID No: 3) where "Pal" corresponds to diaminopropionic acid, which is a nonhydrolyzable palmitate group that is covalently attached to a diaminopropionic acid functionality, and in this example synthesized into the peptide backbone. The initial tryptophan residue in Palm-1 provides an aromatic ring structure for monitoring by absorption spectroscopy, and it not believed to be crucial to the function of the peptide. A nonspecific peptide with the sequence H6SLGAAAGSGC (providing a general structure of H6-spacer-cysteine) (SEQ ID No: 8) was labeled with Cy3-maleimide ($\lambda$abs 550 nm/$\lambda$em 570 nm, GE Healthcare, Piscataway N.J.) on the terminal cysteine residue and used for FRET studies. The peptides were synthesized using Boc-solid phase peptide synthesis, purified by HPLC, and characterized by electrospray ionization mass spectrometry (see references 13 and 19). Preparation of the nonhydrolyzable palmitate group that is covalently attached to a diaminopropionic acid functionality synthesized into the peptide backbone can be accomplished by one of ordinary skill in the art, as described in reference 48.

Cell Culture.

Human embryonic kidney (HEK 293T/17) and African green monkey kidney (COS-1) cell lines (ATCC, Manassas, Va.) were cultured in complete growth medium (Dulbecco's Modified Eagle's Medium (DMEM; purchased from ATCC)) supplemented with 1% (v/v) antibiotic/antimycotic and 10% (v/v) heat inactivated fetal bovine serum (ATCC). Cells were cultured in T-25 flasks and incubated at 37° C. under 5% CO2 atmosphere and a subculture was performed every 3-4 days (see reference 13).

Cellular Delivery of Quantum Dots.

The QD delivery experiments were performed on adherent cells seeded into the wells of Lab-Tek 8-well chambered #1 borosilicate coverglass (Nalge Nunc, Rochester, N.Y.) coated with 2 µg/mL fibronectin. For electroporation and nucleofection, adherent cells were harvested by trypsinization prior to performing QD delivery to cells in suspension. Cells were then seeded to chambered coverglass wells and imaged after cell attachment. The endosomal marker AlexaFluor647-transferrin was included as indicated in the text. For imaging, cells were washed with phosphate buffered saline (PBS, 137 mM NaCl, 10 mM phosphate, 3 mM KCl, pH 7.4), fixed with 3.7% paraformaldehyde in PBS and nuclei were stained with DAPI (Sigma) unless otherwise indicated.

Comparative Example

Electroporation and Nucleofection of QDs

For electroporation, cells were harvested by trypsinization and recovered for 1 hour in complete growth medium, pelleted, and resuspended in PBS. 510 nm DHLA-PEG QDs (0.5 µM final concentration) were mixed with 1×104 cells to a final volume of 100 µL in PBS in a 0.2 mm electroporation cuvette. The cuvette was subjected to 100 V for a 20 ms pulse using a GenePulser XCell electroporator (Bio-Rad, Hercules, Calif.). Cells were resuspended in complete growth medium, seeded into fibronectin-coated 8-well chambered coverglass, fixed and imaged after 24 hrs. For nucleofection delivery, 1×10$^6$ cells were harvested and resuspended in 100 µL of NUCLEOFECTOR reagent (Amaxa, Gaithersburg, Md.). 510 nm DHLA-PEG QDs were included at a final concentration of 0.4 µM. The cell/QD/reagent mixture was pulsed in the NUCLEOFECTOR using a preset protocol adapted for each specific cell line (20, 21). Cells were cultured and imaged as described for electroporation. As a positive control, a plasmid encoding monomeric red fluorescent protein (RFP) was delivered using the same conditions as those for QD delivery and positive expression of the RFP confirmed.

Comparative Example

INFLUX-Mediated Delivery

The INFLUX cell-loading reagent mediates the intracellular release of materials internalized via pinocytic vesicles by delivering the materials to cells in a hypertonic medium followed by the transfer of the cells to a hypotonic medium to induce vesicle disruption (see reference 22). 510 nm DHLA-PEG QDs were diluted to a final concentration of 300-800 nM in the supplied hypertonic delivery media according to manufacturer's instructions and incubated on the cells for 30 min at 37° C. The hypertonic medium was exchanged for hypotonic medium (serum-free culture medium diluted by 40% with deionized water) and incubated on the cells for 3 min. The cells were then recovered in complete growth medium for 30 min and cultured for various lengths of time prior to washing and fixation for imaging.

Comparative Example

Lipofectamine 2000™-Mediated Delivery 520 nm QDs with a 1:1 mixed surface of DHLA:DHLA-PEG were incubated with LIPOFECTAMINE 2000 for 20 min in serum free medium at a ratio of 1 µL LIPOFECTAMINE 2000 per 1.5 pmol QD. The complexes, at a final QD concentration of 75 nM, were incubated with the cells for 4 hours, removed and replaced with complete growth medium. The cells were then cultured for 24-36 h prior to washing and fixation.

Comparative Example

Polyethyleneimine-Mediated Delivery

PEI was incubated with 520 nm mixed surface DHLA:DHLA-PEG QDs in serum free medium at a ratio of 10 µg PEI per 1 pmol QD for 15 min. This ratio was previously determined in delivery experiments to yield maximal QD uptake. The complexes were then diluted into serum free media to a final QD concentration of 75-100 nM, incubated with cells for 2 h and removed. Cells were then cultured in complete media for 24-36 h, washed and fixed.

Comparative Example

PULSin™-Mediated Delivery

A stock solution of 520 nm DHLA:DHLA-PEG QDs (1 µM in 0.1 M borate buffer, pH 8.9) was diluted to 0.5 µM in HEPES (4-(2-hydroxyethyl)-1-piperazineethanesulfonic acid, pH 8.2). PULSin™ delivery reagent was added (1 µL per 20 pmol QD) and complex formation occurred for 20 min at 25° C. The complexes were diluted into serum free medium to a final QD concentration of 100 nM and incubated on cells for 1-3 h after which complexes were removed and replaced with complete growth medium. Cells were subsequently cultured for up to 5 days to monitor intracellular QD distribution.

Inventive Example

Peptide-Mediated Delivery

QD-CPP, QD-NLS and QD-Palm-1 bioconjugates were formed by diluting a stock solution of preformed peptide-QD complexes (1 µM QD assembled with 25 CPP, 30 NLS or 75 Palm-1 peptides per QD in 0.1 M borate buffer, pH 8.9) into complete growth medium to a final QD concentration of 50-100 nM. These peptide:QD ratios were determined experimentally for each peptide to be that ratio that yielded a high degree of cell uptake. The self-assembled bioconjugates were then incubated with cells as described elsewhere herein. For monitoring the intracellular fate of QD-CPP assemblies, AlexaFluor 647-transferrin, LysoTracker Red DND-99 and BODIPY TR-ceramide-BSA subcellular markers were included at the manufacturer's recommended concentrations. In some experiments, QD-CPP complexes were also incubated with cells in the presence of pyrenebutyrate (100 µM), sucrose (500 mM) or chloroquine (500 µM) to test either membrane translocation or to induce endosomal disruption and release of the internalized QDs to the cytosol. The general scheme for the assembly of QDs with cationic polymers, cationic amphiphiles or histidine-tagged peptides is shown in FIG. 1B.

Microscopy and Image Analysis.

The intracellular distribution of QDs was analyzed by differential interference contrast (DIC) and epifluorescence microscopy using an Olympus IX-71 total internal reflection fluorescence microscope equipped with a 60× oil immersion lens. Samples were excited using a Xe lamp and images were collected using standard filter sets for DAPI, FITC (for QDs), TRITC (for Cy3 and Texas Red) and Cy5 (for AF647-transferrin). Merged images were generated using Adobe PhotoShop. Förster resonance energy transfer (FRET) measurements for determining the intracellular stability of QD-peptide association over time were performed by imaging 510 nm donor QD-CPP conjugates decorated with approximately 2 Cy3-labeled acceptor peptides per QD. The Förster radius (R0) for this donor-acceptor pair is approximately 47 Å. Side-by-side split fluorescence images were collected and quantitated using a DualView system (Optical Insights, Tucson, Ariz.) equipped with a 565 nm dichroic filter. The QDs and Cy3 were excited at 488 nm and their respective emissions were separated with the dichroic filter and deconvoluted. Signal intensities were measured at various time points over a three day period to calculate the Cy3/QD emission ratio (defined as [Cy3em/Cy3em+QDem]). This ratio corrects for any direct excitation of the Cy3 dye which may occur intracellularly (see reference 23). To correct for any leakage of the QD signal into the Cy3 channel, this ratio was also calculated for cells exposed to QD-CPP alone (no Cy3-labeled peptide) and subtracted from the Cy3/QD emission ratio to give the corrected ratio ([Cy3em/Cy3em+QDem]−QDem). A decrease in this ratio over time indicates either the dissociation of the Cy3-labeled peptide from the QD surface or degradation of the Cy3 fluorophore.

Cytotoxicity Assays.

Cellular toxicity was assessed using the CellTiter 96 Cell Proliferation Assay (Promega, Madison Wis.) according to the manufacturer's instructions. This assay is based upon the conversion of a tetrazolium substrate to a formazan product by viable cells at the assay end point (see reference 24). Cells ($1 \times 10^4$ cells/well) were cultured in 96-well microtiter plates in complete growth medium in the presence of increasing concentrations of QDs, free peptide or polymer, or QDs in complex with peptide or polymer. In each case, the materials were incubated with the cells for the time required for efficient QD uptake. The materials were subsequently replaced with complete growth medium and the cells were cultured for 72 hours.

Long-Term Intracellular Fate of QD-CPP Conjugates.

Figure 2A:
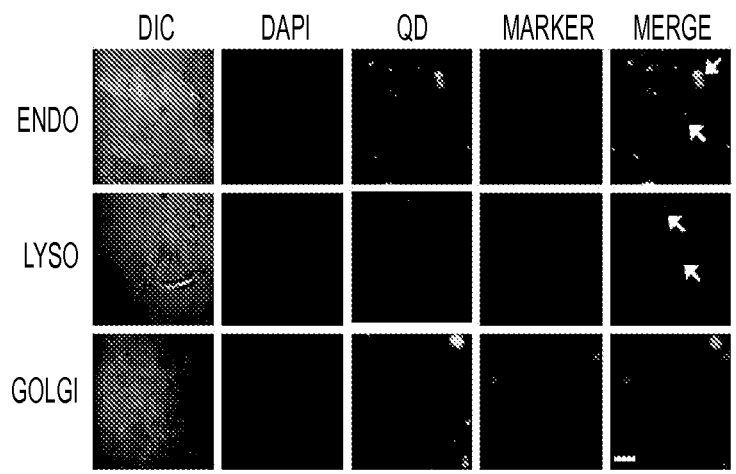
FIGS. 2A and 2B show
Figure 2B:
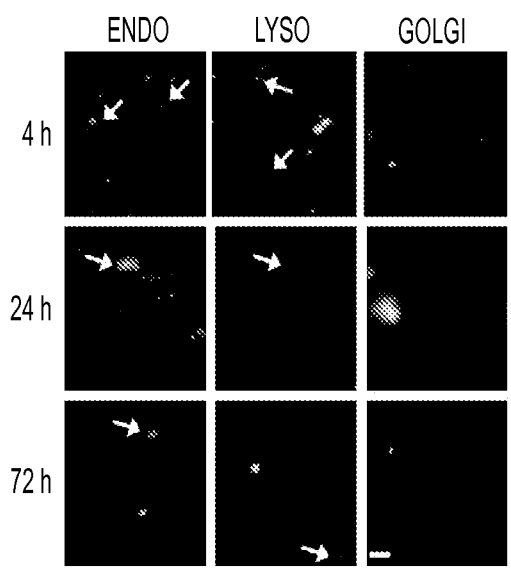

The intracellular fate of the delivered QD-CPP complexes was followed at various time points in cell culture. HEK 293T/17 cells were incubated with DHLA-capped 510 nm QDs complexed with the CPP while counter-labeling either the endosomes (AlexaFluor 647-transferrin), lysosomes (LysoTracker Red DND-99), or the Golgi complex (BODIPY TR-ceramide-BSA). As shown in FIG. 2A, one hour post-delivery the QDs adopted a punctate, vesicular appearance with QD fluorescence in green overlapping the endosome and lysosome markers, while no overlapping QD signal was observed with the Golgi complex markers. This confirms that the QD-CPP complexes were located within the endolysomal system in agreement with previous results observed by the present inventors. Similar data was collected for cells exposed to QD-CPP complexes and the same markers at 4, 24 and 72 hours after delivery, as seen in FIG. 2B. After 3 days, the QD-CPP complexes still colocalized with the endolysosomal markers although it is noted that at the later time points, the QD distribution appears to be primarily perinuclear probably reflecting that these are later or more 'mature' endosomes. When the cells were cultured beyond 3 days, similar results were obtained. These results demonstrate that while the CPP mediates the efficient uptake of the QDs, it does not facilitate the release of the QDs to the cytosol over time. Similar data were obtained with DHLA-PEG capped QDs showing that the nature of the capping ligand, i.e., charged vs. neutral, had no effect on intracellular QD fate over time.

Intracellular Stability of QD-CPP Assemblies.

For the successful implementation of QD-peptide and QD-protein conjugates in intracellular applications, it is desirable for them to exhibit long-term stability during and after uptake by the cell. For example, labeling specific subcellular organelles such as mitochondria or the nucleus with QD-peptide conjugates requires the stable association of the targeting peptide with the QD surface throughout the uptake and targeting process. Of particular interest in the case of the self-assembled QD-CPP described herein (generated by polyhistidine-zinc interactions) is the conjugate stability within the endolysosomal vesicles during the three day culture period. Given that the normal pKa of histidine residues is ~6.5 and that the pH of the vesicles can drop to as low as ~5.0 to 5.5 during the formation of late endosomes and lysosomes (see reference 28), protonation of the imidazole side chains of the polyhistidine tract could result in dissociation of the CPP from the QD surface. Alternatively, several proteases including cathepsins and several aspartate proteases are endogenously expressed in the endolysosomal system and these may also proteolyze the peptides (see reference 29). Thus, confirmation of the long-term intracellular stability of QD-CPP assemblies was warranted.

Figure 3A:
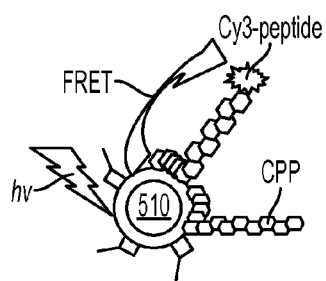
FIGS. 3A through 3D show shows the intracellular stability of polyhistidine-QD association. For FIG. 3A 510 nm dihydrolipoic acid (DHLA) QDs were appended with 25 CPP to mediate uptake in HEK 293T/17 cells and ~2 Cy3-labeled peptides to monitor the FRET between the QD and the Cy3 dye over time.
Figure 3B:
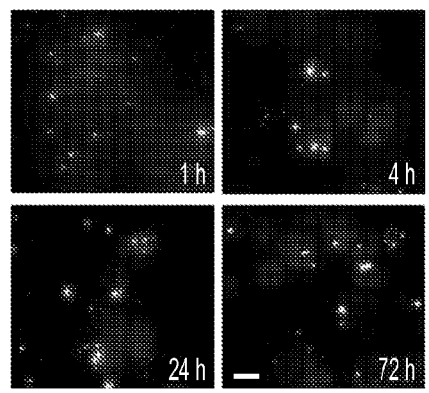
Figure 3C:
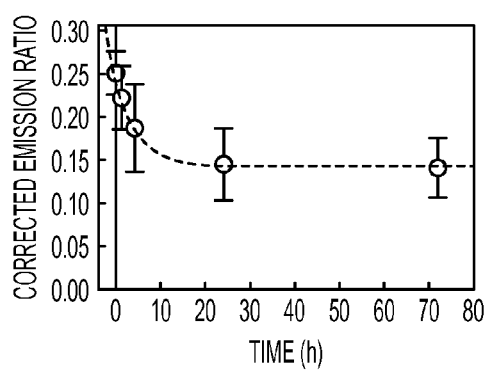
Figure 3D:
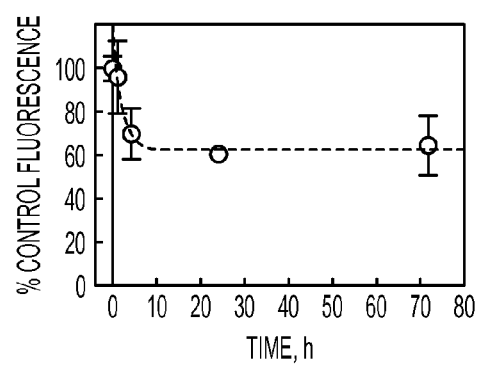

To investigate this issue, QD-peptide conjugates were prepared that engaged in FRET and their intracellular interactions were monitored over time. 510 nm DHLA-capped QDs were first assembled with an average of ~2 Cy3-labeled $His_6$-peptides and then the CPP was added to form the full conjugate (schematic in FIG. 3A). Due to the peptide's small size and proximity of the Cy3 acceptor to the nanocrystal surface, this valence results in a ca. 40% quenching of the QD PL by FRET. The resulting conjugates were delivered to HEK 293T/17 cells and the cells were cultured for three days. QD-donor and Cy3-acceptor FRET interactions over time within the cells were measured by exciting the QD and collecting side-by-side split fluorescence images using the DualView system and deconvoluting the subsequent intensity data. The excellent spectral separation (~60 nm) between the QDs and Cy3 emission maxima facilitated this collection. FIG. 3B shows representative images in which the QD and Cy3 signals are merged at various time points during the culture period. A distinct one-to-one overlap in the punctate signals of both QD and dye was observed demonstrating colocalization of the QDs and Cy3-labeled peptides within endocytic vesicles throughout the culture period. Analyses of the signals showed the pair was actively engaged in FRET (close proximity) and not just present within the same endosomal compartments. When the Cy3/QD emission ratio (normalized and corrected for direct Cy3-acceptor excitation) was calculated a gradual decrease was observed over time, culminating in a 36% decrease over three days (FIG. 3C). A decrease in this ratio would result from either Cy3-peptide dissociation from the QD surface (loss of $His_6$ interactions or proteolysis) or by chemical degradation of the dye. Control experiments revealed that the latter scenario was the case. When Cy3 was delivered to the endosomes as a Cy3-labeled transferrin conjugate (no QDs present), the fluorescence output of the dye decreased approximately 34% over the same time period, in excellent agreement with the decrease observed in the above QD-CPP-Cy3-labeled peptide constructs (FIG. 3D). Control experiments performed with QD donors alone showed no change in the relative QD PL. These results suggest that the $His_6$-bearing peptides remain stably conjugated to the QD Zn-surface, even within the acidic environment of the endocytic vesicles over time. This strong affinity, even at lower pH, appears to be as a result of cooperative interactions resulting from the multiple histidine residues present on each peptide interacting with the QD surface (see reference 14). Previously, the stability of the QD-peptide conjugates within endosomes had only been verified for one hour after uptake using two-photon excitation FRET microscopy (see reference 23). As best can be determined, presented herein represent the first instance in which the His-zinc interaction has been shown to be stable intracellularly over three days. This finding has important implications for the use of this QD conjugate assembly strategy in long-term intracellular labeling and imaging applications.

Cytosolic Delivery of QDs.

Figure 4A:
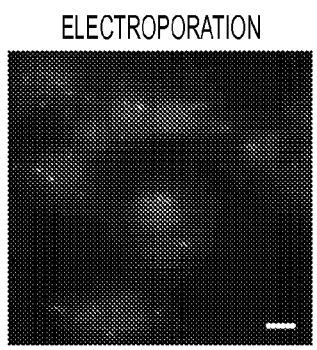
FIGS. 4A-4F show cellular delivery of QDs using various active and facilitated methods. 510 nm DHLA-PEG (dihydrolipoic acid-polyethylene glycol) QDs at a concentration of 400-500 nM were delivered to HEK 293T/17 cells by electroporation in FIG. 4A or nucleofection in FIG. 4B.
Figure 4B:
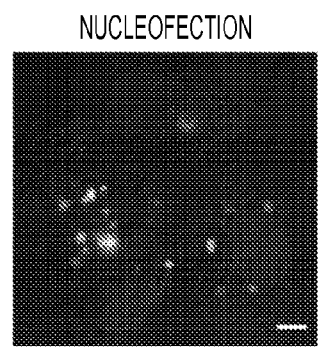

Having confirmed the long-term sequestration of QDs within endosomes following CPP-facilitated uptake, a means by which to deliver QDs to the cytosol was sought. Thus began an exhaustive investigation of methodologies to either: (1) deliver the QDs directly to the cytosol via direct physical manipulation of the cell (active delivery), or (2) decorate the QDs with peptides or polymers that could mediate both endocytic uptake and the subsequent release of the QDs from within endocytic vesicles (facilitated delivery followed by endosomal escape). The individual approaches are summarized in Table 1 and the results of the various methods tested are discussed in the following sections.

ability of the membrane's phospholipid bilayer allowing charged extracellular materials to directly enter the cytosol during an electric pulse (see reference 30). Nucleofection further incorporates a proprietary transfection reagent to mediate the subsequent localization of internalized materials to the nucleus (see references 20 and 21). As shown in FIGS. 4A and 4B, when 510 nm DHLA-PEG capped QDs were delivered to HEK 293T/17 cells using electroporation or nucleofection, they adopted a punctate morphology indicative of QD aggregation within the cytosol. This delivery bypassed the endosomes as confirmed by transferrin counterstaining. In contrast, when QDs capped with these same ligands were microinjected into cells, they adopted a highly disperse staining across the entire cytosol for long periods of time (see reference 18). This indicates that the electric field and/or process itself adversely affects subsequent intracellular QD solubility. Further, no evidence of nuclear accumulation or localization within the perinuclear spaces was observed even after extended culture following delivery for both methods. Also noted was a high degree of cell death and estimate that only 50% of cells remained viable following delivery attempts.

Electroporation-based QD delivery has yielded similar results in previous reports (see references 31 and 32). Cumulatively, the QD aggregation and subsequent high cellular morbidity suggest that electroporation and nucleofection are not effective means of delivery despite their ability to deliver QDs directly to the cytosol.

Facilitated Delivery.

Facilitated delivery of QDs involves the use of exogenous agents that are added to the extracellular medium or complexed with the QDs to exploit the cell's innate processes of pinocytosis or endocytosis. Pinocytosis, or fluid-phase

TABLE 1

Summary of QD Delivery Strategies Examined Herein

| Delivery Method/Agent | Mechanism of Uptake | Quantum Dot Fate and Toxicity |
| --- | --- | --- |
| Active Delivery | | |
| Electroporation | Membrane pore formation | Poor uptake, QDs aggregated, toxic[a] |
| Nucleofection | Membrane pore formation | Poor uptake, QDs aggregated, toxic[a] |
| Facilitated Delivery | | |
| Pinocytosis | | |
| Influx ™ | Pinocytosis | Endosomal, QDs punctate, moderately toxic[a] |
| Polymer-mediated | | |
| Lipofectamine2000 ™ | Endocytosis | Endosomal, QDs punctate, toxic[b] |
| Polyethyleneimine | Endocytosis | Endosomal, QDs punctate, toxic[a] |
| PULSin ™ | Endocytosis | Cytosolic, QDs dispersed, toxic[b] |
| Peptide-mediated | | |
| CPP peptide | Endocytosis | Endosomal, QDs punctate, minimally toxic[b,c] |
| NLS peptide | Endocytosis | Endosomal, QDs punctate, minimally toxic[b] |
| Palmitoylated peptide (Palm-1) | Endocytosis | Cytosolic, QDs dispersed, minimally toxic[b] |
| Augmented peptide-mediated | | |
| CPP peptide + sucrose | Endocytosis | Cytosolic, QDs punctate, toxic[a] |
| CPP peptide + chloroquine | Endocytosis | Cytosolic, QDs punctate, toxic[a] |
| CPP peptide + pyrenebutyrate | Membrane translocation | Mixed membranous and endosomal, toxic[a] |

[a]General toxicity assessment made by visual inspection of cellular morphology and rate of proliferation compared to control cells during delivery experiments.
[b]Toxicity measured by cell proliferation assay as described elsewhere herein.
[c]Toxicity reported in reference 13.

Active Delivery.

Electroporation and nucleofection are primarily used for the cellular delivery of nucleic acids and employ an externally applied electric field to increase the excitability and permeability of the membrane's phospholipid bilayer allowing uptake, is a nonspecific form of endocytosis in which minute amounts of extracellular fluids and materials are internalized within small vesicles. Endocytosis, in contrast, is a specific process as the uptake of extracellular materials is mediated by their interaction with cognate cell surface receptors that become spatially concentrated within the forming endocytic transport vesicles (see references 33 and 34). The exogenous agents for facilitated delivery can take the form of chemicals or drugs that are co-incubated with the QDs during the delivery process or alternatively they can be polymers or peptides that are either covalently attached or non-covalently associated (electrostatically) with the QD surface.

Pinocytosis-Mediated Delivery.

Figure 4C:
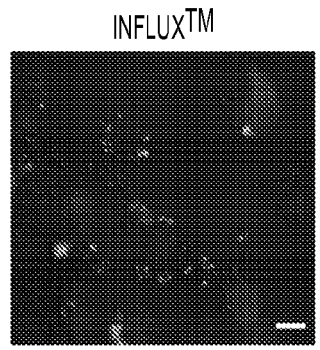

To exploit this process, the commercial pinocytosis reagent known as Influx™ was used. This reagent is co-incubated with the QDs and cells in a hypertonic medium which promotes the uptake of extracellular materials within pinocytic vesicles. The cells are then briefly incubated in a hypotonic medium to swell and disrupt the vesicles, releasing the internalized materials into the cytosol; in essence this is a modified intracellular osmotic shock protocol. A solution of 510 nm DHLA-PEG QDs was prepared in the hypertonic delivery media (including the Influx™ reagent) and incubated with HEK 293T/17 cells for the recommended period of time for uptake (~30 min). As shown in FIG. 4C, only a modest degree of uptake occurred even when the QD concentration was substantially increased to 800 nM. Further, the intracellular QD morphology remained punctate even after several days, indicating their persistent localization within pinocytic vesicles. Jaiswal et al. also reported the long-term intracellular sequestration of pinocytically delivered QDs (see reference 6). In that study, 400 to 600 nM negatively charged DHLA-capped CdSe/ZnS QDs were incubated with HeLa cells for 2-3 hrs without any exogenous pinocytosis reagent present: using a plasmid-expressed fluorescent protein endosomal marker for counter-labeling, the QDs remained trapped within vesicles for up to nine days in culture.

Polymer-Mediated Delivery.

Figure 4D:
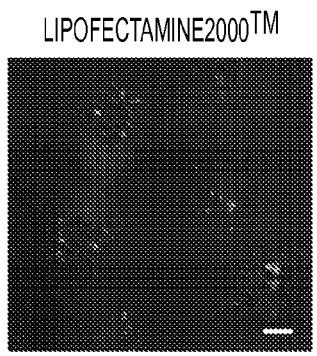

A number of commercial cationic polymers have been developed for gene delivery and transfection applications. These reagents self-assemble electrostatically to negatively-charged species (e.g., nucleic acids) while simultaneously mediating interactions of the resulting complex with the plasma membrane to induce endocytosis. Once compartmentalized within intracellular vesicles, it is believed that the cationic polymers can facilitate endosomal disruption via osmotic lysis (the 'proton sponge' effect), releasing the vesicle contents to the cytosol (see references 35 and 36). It was hypothesized that QDs bearing a net negative surface charge could complex with such polymers and thus utilized 520 nm QDs capped with a 1:1 mixed surface of DHLA:DHLA-PEG ligands. This cap exchange strategy provides both a charged moiety (DHLA) along with the extended pH stability provided by the PEG ligands (see references 18 and 37). Initial experiments utilized the well-known cationic liposomal transfection reagent Lipofectamine2000™. QD-Lipofectamine complexes were formed as described in the Methods section and incubated with HEK 293T/17 cells for 4 hours. As shown in FIG. 4D, it was found that the QDs were completely colocalized with the co-delivered transferrin endosomal marker. Extended monitoring of the cells for several days after delivery did not reveal any changes in this morphology. Interestingly, Derfus et al., demonstrated that commercial PEG-coated QDs delivered to HeLa cells using this reagent appeared to be largely present within the cytosol (see reference 31). However, their interpretation was complicated by the fact that the QDs also formed aggregates of several hundred nanometers in diameter within the cytosol and were not well dispersed. It was not apparent if the liposomal polymer was responsible for inducing the intracellular QD aggregation in this case.

Figure 4E:
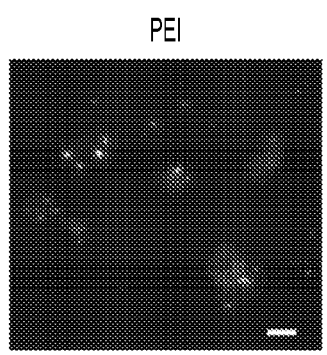

Polyethyleneimine (PEI) is a cationic polymer that is sometimes used as a reagent for transfecting nucleic acids into mammalian cells and has recently been used for cellular uptake of QDs. Duan et al. synthesized dendritic PEG-grafted PEI ligand molecules and used them to functionalize CdSe—CdS—ZnS QDs (see reference 38). They demonstrated that this specific combination of surface chemistries could mediate both endocytosis and subsequent cytosolic delivery of these QDs to HeLa cells. They found that the efficiency of QD endosomal escape was enhanced by increasing the PEI content in the PEG-PEI ligand. However, the increased PEI content was also coupled with significant cytotoxicity as cellular viability dropped to only 40% with this more efficient endosomal escape capping ligand. The combination of PEG and PEI was tested for cellular uptake by complexing 520 nm QDs capped with 1:1 DHLA:DHLA-PEG ligands with increasing ratios of PEI (~0.5-10 µg PEI per 1 pmol QD) and then exposing them to HEK 293T/17 cells for 1-3 h. As demonstrated by the representative micrograph in FIG. 4E, complete colocalization of the QDs with the transferrin marker within endosomes was noted at each concentration tested even after several days. Similarly, a considerable degree of cytotoxicity was noted that tracked the increasing concentrations of PEI used to form the QD-PEI complexes.

Figure 4F:
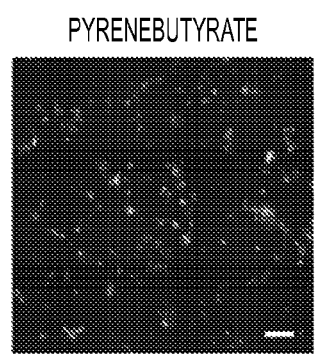

Jablonski et al. reported the ability to rapidly deliver polyarginine peptide-bearing QDs directly to the cytosol using an excess of the hydrophobic counterion, pyrenebutyrate (see reference 39). Using streptavidin conjugated QDs assembled with biotinylated polyarginine peptides in the presence of >1,000 fold molar excess pyrenebutyrate (4 µM) per QD (4 nM), delivery of the QDs (~5 min) to BS-C-1 monkey kidney cells appeared to produce QDs dispersed within the cytosol. Those authors surmised that the anionic pyrenebutyrate bound to the cationic polyarginine to form a hydrophobic polymeric complex that could pass directly through the plasma membrane. However, when HEK 293T/17 cells were incubated with 550 nm DHLA-PEG QD-CPP assemblies (100 nM in QDs) in the presence of a far higher concentration of pyrenebutyrate (100 µM), the QDs initially remained entirely associated with the plasma membrane even after a ~6× longer incubation of 30 min. After 3 hours, the QDs took on a punctate appearance, indicative of endosomal uptake and no cytosolic dispersal was observed (see FIG. 4F). Thus, the results reported Jablonski et al. (reference 39) cells were not reproduced by the present inventors. It remains unclear what role pyrenebutyrate plays in the uptake process, but these results suggest it is likely that differences in the supplied material (i.e., presence or absence of a covalently attached 60 kDa streptavidin protein along with different surface ligands) may actually play profound part in determining the nature of the interaction of nanomaterials with the plasma membrane.

Figure 5A:
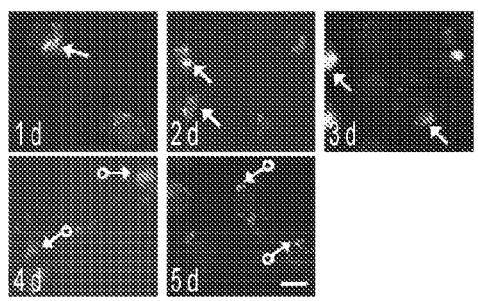
FIGS. 5A-5D show cellular delivery and cytotoxicity of PULSin™-QD conjugates. 520 nm 1:1 DHLA:DHLA-PEG mixed surface QDs (100 nM final QD concentration) were complexed with PULSin™ polymer and incubated for 1-3 h with COS-1 cells (FIG. 5A) or HEK 293T/17 cells (FIG. 5B). Shown are images in which the DAPI, QD and AlexaFluor 647-transferrin images are merged at 1d, 2d, 3d, 4d and 5d post-QD delivery. Regular arrows denote areas of colocalization between the QDs and endosomes (a yellow color was noted, indicating merged QD and transferrin signals). Open circle-terminated arrows indicate areas where the QD signal is separated from the endosomal marker. The scale bar is 10 µm. Cytotoxicity data demonstrating the effects of the PULSin™-QD complexes on cellular proliferation are shown for COS-1 (FIG. 5C) and HEK 293T/17 cells (FIG. 5D). Cells were incubated with the complexes for 3 h, washed and subsequently cultured for 72 h prior to viability assay. When the QDs are present, the concentration given is that of the QDs. Each data point represents the mean±SD of triplicate measurements
Figure 5C:
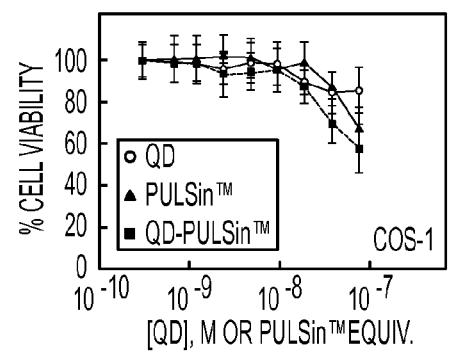
Figure 5B:
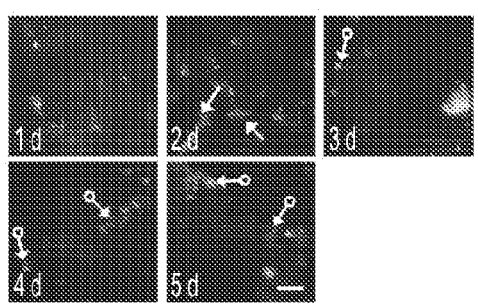

Another molecule was tested in this class of materials, namely the commercially available PULSin™, a proprietary amphiphilic polymer originally designed as a cytosolic delivery agent for proteins. It was found that PULSin™ could mediate efficient uptake of QDs and a modest subsequent endosomal release to the cytosol over a much longer time period of 3-4 days. As shown in FIGS. 5A and 5B, PULSin™ complexation resulted in initial endosomal uptake of 520 nm DHLA:DHLA-PEG QDs to both COS-1 and HEK 293T/17 cells after 1d incubation. Following uptake, the cells were allowed to grow continuously for 5 days and samples were imaged throughout. Approximately three to four days after the initial delivery, the QD signal began to separate from that of the endosomal marker, indicating endosomal escape in both cell lines. By day 5, the QDs had assumed a slightly more dispersed intracellular appearance that was completely distinct from that of the endosomes which had a more perinuclear localization. Longer incubation times did not improve on these results. The results were rather modest in terms of overall cellular labeling efficiency, but it was clear that combining PULSin™ with mixed surface QDs could facilitate some endosomal escape. However, in addition to requiring several days to mediate endosomal escape of the QDs, PULSin™ also elicited a considerable degree of cytotoxicity in both cell lines (FIGS. 5C and D). It was found that the toxicity was attributable to the PULSin™ polymer alone. When cells were incubated with 100 nM mixed surface QDs alone, the viability of both COS-1 and HEK 293T/17 cells was approximately 80% while in the presence of either PULSin™ alone or QD-PULSin™ complexes, cell viability was reduced to less than 60%.

Peptide-Mediated Delivery.

The use of peptides still remains the most popular means of facilitated QD delivery (see reference 10). In this case, the QDs are decorated with a peptide that induces endocytosis by mediating interaction with specific cell surface receptors or more generally through electrostatic interactions with the cell surface (see reference 40). For electrostatic interactions, peptides derived from the HIV-1 Tat protein have been used.

Sucrose and chloroquine are two well known endosomolytic agents that have been shown to facilitate the release of endocytosed nucleic acids to the cytosol (see reference 43). Sucrose accumulates within endocytic vesicles and promotes vesicle swelling and destabilization (see reference 44). Chloroquine is an endolysosomal-tropic amine whose buffering capacity prevents endosomal acidification and slows down the rate of endocytosis, allowing more time for endosomal escape (see reference 45). In this instance, 510 nm DHLA-PEG QDs were self-assembled with CPP and incubated with HEK 293T/17 cells for 2-3 h in the presence of increasing concentrations of either agent up to a maximum of 500 mM sucrose or 500 µM chloroquine. Both compounds efficiently disrupted the endosomes at the highest concentrations as evidenced by the diffuse appearance of labeled transferrin in the cytosol. The QDs, however, remained punctate in appearance and were not well-dispersed despite the presence of the far more soluble PEGylated QD ligands (see reference 18). Also noted were significant cellular toxicity and morbidity, especially as the concentrations of each agent were increased.

Nuclear localization signal (NLS) peptides bearing a sequence derived from the simian virus 40 T-antigen have been reported to mediate QD uptake and subsequent nuclear delivery (see reference 46). Rozenzhak and co-workers utilized commercial Streptavidin functionalized QDs assembled with biotinylated NLS peptides and incubated with a secondary non-covalent peptide carrier (Pep-1) to create complexes for delivery to HeLa cells. They found a high degree of subsequent QD colocalization with the nuclear stain DAPI and little residual cytosolic or endosomal staining. Thus, in a conjugation approach similar to that used for the CPP, as described herein a histidine-tagged NLS peptide was assembled onto the surface of QDs for delivery experiments. When incubated with HEK 293T/17 and COS-1 cells, however, the QDs were found to be completely internalized within endosomes, with no release to the cytosol or nuclear translocation observed even after culturing the cells for two days after QD uptake.

Furthermore, the use of a multifunctional peptide including a portion originally intended for the delivery of protein palmitoyl transferase 1 (PPT1) inhibitors across the blood-brain barrier was tested (see references 47 and 48). This peptide, WG(Pal)VKIKKP$_9$GGH$_6$ (referred to as Palm-1 and having SEQ. ID. No. 3), encompasses several different modules or domains each of which provides one or more overlapping functionalities. The peptide includes a His$_6$ tag to mediate self-assembly to the QD surface. The di-glycine residues were placed into the sequence to act as a flexible spacer between the His$_6$ domain and the rest of the peptide once it coordinates to the QD surface. Adjacent to the polyhistidine domain is a repeat of nine consecutive proline residues. Studies have shown that poly(L-proline) sequences adopt a left-handed helical structure of 3.1 residues per turn in aqueous solvent, referred to as the polyproline II or PPII motif (see reference 49). Nine prolines are predicted to assume a PPII structure with a length of ~28-30 Å, thus this sequence was utilized as an extended spacer to allow the rest of the peptide sequence to extend out beyond the PEGylated shell surrounding the QD (assumed length of ~30-35 Å in an energy minimized state). PPII motifs also possess amphiphilic properties. Peptides containing proline repeats of various lengths have been used in relation to the cellular uptake of attached fluorophores (see references 50-52), DNA-lipid complexes (see reference 53) and gold nanoparticles (see reference 54). The VKIKK motif (SEQ ID No: 7) is derived from a sequence found at the C-terminus of the K-Ras protein (V-Ki-ras2 Kirsten rat sarcoma viral oncogene homolog) (see reference 55). This Ras family homologue is a membrane-tethered GTPase that functions in many overlapping signal transduction pathways. The KKIK portion (SEQ ID No: 42) is thought to mediate electrostatic interactions with lipid head groups on the cytosolic leaflet of membranes displaying negatively charged phosphatidylserines. Similar to the positive charges resident within the Tat and NLS sequences, the three positively charged lysines may also facilitate the peptide's initial electrostatic interaction with negative charges on the cellular membrane. In the K-Ras protein, the VKIKK (SEQ ID No: 7) sequence is preceded by a cysteine residue that is normally post-translationally modified with a palmitoyl group which can also be depalmitoylated by PPT1 in the lyososome. Due to its highly hydrophobic nature, the palmitoyl group inserts into the membrane allowing the full K-Ras (or similar post-translationally modified proteins), to remain membrane-bound (see references 56-58). Rather than attaching the palmitoyl group in the peptide to a cysteine residue which would leave it vulnerable to PPT1 cleavage in the endolysomal system, it was decided to covalently attach it to a synthetic diaminopropionic acid (Dap) residue, thus rendering it nonhydrolyzable. It was conceived that by using a peptide incorporating multiple overlapping functional sequences shown to facilitate both endocytosis and intracellular membrane interactions, cytosolic delivery of the QDs could be achieved.

Figure 6A:
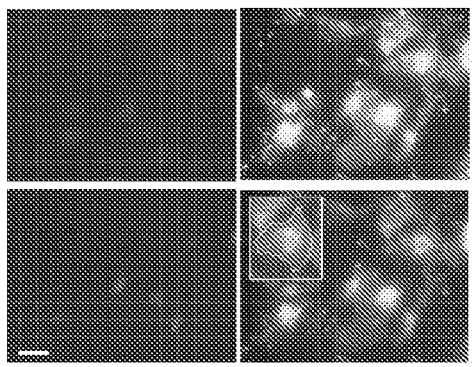
FIGS. 6A-6D show shows the cellular delivery and cytotoxicity of Palm-1 peptide (SEQ ID No: 3) conjugates with quantum dots. 550 nm DHLA-PEG QDs were decorated with the Palm-1 peptide, incubated for 1-2 h along with AlexaFluor 647-transferrin, and imaged at 48 h post-delivery within COS-1 in FIG. 6A or HEK 293T/17 cells in FIG. 6B. The inset in the merged images shows a single cell with the cell membrane highlighted for clarity.

COS-1 and HEK 293T/17 cells were incubated for 1-2 h with 550 nm DHLA PEG QD-Palm-1 complexes in the presence of AlexaFluor 647-transferrin. Imaging the cells at 1 hr post delivery revealed that the QD complexes were internalized with a punctate appearance that was completely colocalized with the endosomal marker confirming endocytic uptake. As shown in FIGS. 6A and B, approximately 48 h post-delivery the QD signal separated from that of the endosomal marker in both cell lines and the QDs became well-dispersed, occupying the entire cell volume. Greater than 90% of cells observed were positive for initial QD uptake and of those, 77% showed a high degree of endosomal escape. Although a small degree of endosomal escape was observed at 24 h, QD release from endosomes was maximal at 48 h post-delivery and no appreciable increase in escape efficiency was noted at 72 h or longer. Some punctate areas of brighter QD fluorescence remained which were still colocalized with the transferrin, leading us to conclude that not all endosomal QDs were released with this peptide.

Figure 5D:
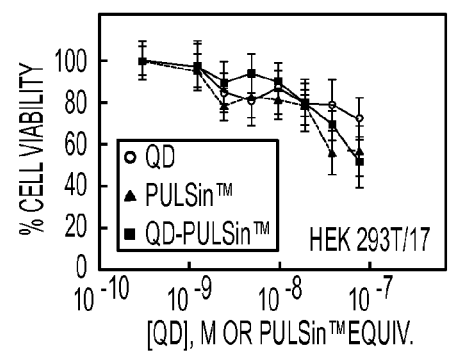
Figure 6C:
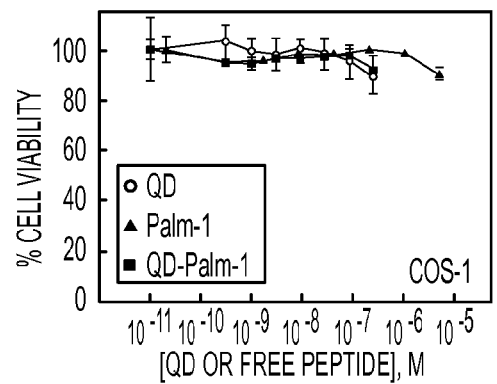
Figure 6B:
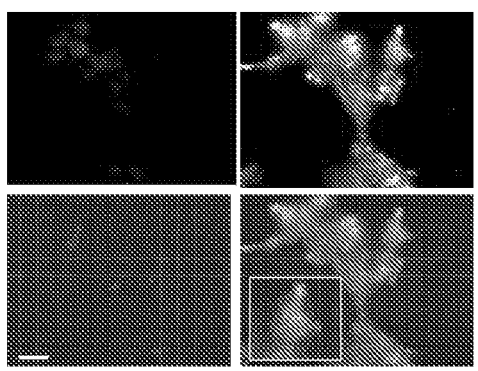
Figure 6D:
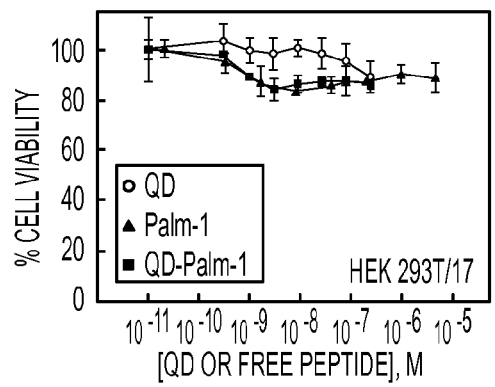

Two further Palm-1 peptide variants were tested; one bearing only a single proline residue and another having no proline residues, termed Palm-2 and Palm-3: in both cases, these resulted in a significant reduction in the degree of endocytic uptake and the QDs remained completely sequestered within endosomes over similar 72 h observation periods (see below for comparison of these Palm peptide sequences). This suggests that while the PPII motif may play a contributing role in mediating more efficient QD uptake by endocytosis, it is absolutely necessary for promoting QD release to the cytosol in both cell lines. Studies in HeLa cells have pointed to a role for polyproline domains in mediating the uptake and cytosolic delivery of peptides containing a combination of proline repeats and various fatty acyl moieties (see reference 51), both features that are present within the Palm-1 peptide. However, the specific mechanism by which the polyproline domain within the Palm-1 peptide mediates uptake and eventual endosomal escape remains unclear. It may provide these critical functions by serving as a spacer that extends the VKIKK sequence (SEQ ID No: 7) and the palmitoyl group beyond the PEG surface, by contributing amphiphilic properties, some combination of both, or by another as yet unidentified role. Significantly, it was found that the QD-Palm-1 complexes elicited minimal cytotoxicity following uptake and endosomal escape, as seen in FIGS. 6C and 6D. In both COS-1 and HEK 293T/17 cells, at the QD-Palm-1 complex concentration required for efficient cytosolic delivery (100 nM), cell viability was greater than 85% even after 3 days. This value is quite close to the minimal cytotoxicity that was noted for delivering QD-CPP complexes to cells with short 1 hr incubations in previous study where the QDs remained sequestered within the endosomes (see reference 13). Thus, although the QDs are escaping from the endosomes with high efficiency, the finding of low concomitant cytotoxicity suggests that the integrity of the endolysosomal system is not being compromised in the process and adversely affecting metabolism or viability. Another noteworthy finding from these data is the reduced cytotoxicity of the peptide-free QDs in HEK 293T/17 cells when their surface is capped exclusively with DHLA-PEG ligands (greater than 90% cell viability, FIG. 6D) compared to when a 1:1 surface of DHLA: DHLA-PEG ligands is used (~75% cell viability, FIG. 5D). COS-1 cells, however, did not exhibit this differential cytotoxicity response to the two QD surfaces (FIG. 6C vs. 5C). This result not only demonstrates the important role played by the capping ligand in mediating QD biocompatibility but also points to inherent differences between the two cell lines.

Comparison of Several Palm Peptide Sequences.

Described herein are modular, multifunctional peptides that (1) assemble with nanoparticles (NP) to generate NP-peptide bioconjugates and (2) mediate the cellular uptake and intracellular distribution of the NP-peptide bioconjugates. The peptides are modular and multifunctional in nature, consisting of distinct domains wherein each domain performs a specific function within the NP-peptide assembly. The domains comprise: (1) an NP association domain which mediates the interface of the peptide with the NP surface; (2) a spacer domain to reduce steric hindrance between the peptide and the NP surface; (3) a cellular association/uptake domain (sometimes referred to as the uptake domain) that mediates the interaction of the NP-peptide assembly with the cell membrane and its components (e.g., cell surface receptors) and the internalization of the assembly by the cellular machinery and (4) a "vesicle escape" domain that mediates the escape of the NP-peptide assemblies from within intracellular vesicles of the cellular uptake pathway, resulting in the intracellular distribution of the NPs.

As an example, a multifunctional, modular peptide was used to mediate the intracellular delivery and the ultimate endosomal release of luminescent semiconductor nanocrystals or quantum dots (QDs). The present disclosure is generally applicable to other classes of NPs and nanomaterials (e.g., gold NPs, carbon nanotubes) and is not limited to the decoration of the NP surface with only a single multifunctional peptide species. The generation of NPs bearing ensembles of different peptides wherein each peptide imparts a different biological function is envisioned.

Potential uses of the peptides described herein include application areas where multifunctional NP-peptide assemblies might be employed, including both biological and non-biological applications. These applications include (but are not limited to) NPs assembled with multifunctional peptides for the purposes of: (1) general cellular labeling, (2) labeling of specific subcellular compartments, (3) cellular tagging for the purposes of cell sorting and/or cataloging, (4) drug delivery and drug monitoring, and (5) in vivo imaging. The decoration of nanoparticles (NP) with polymeric molecules (e.g., proteins, peptides, nucleic acids) has been employed extensively to create hybrid functional materials in which the hybrid assembly adopts a functionality that is greater than either of the two individual component materials alone. This "value-added" approach has resulted in the production of nanoparticle assemblies for non-biological applications including chemical sensing and molecular electronics. More recently this approach has been used for biological applications including the in vitro sensing of enzymatic activity and the labeling of prokaryotic and eukaryotic cells. In these approaches, the polymer used to decorate the NP surface has typically been monofunctional in nature (e.g., an antibody that binds to its cognate ligand or a peptide that serves as a substrate for a targeted enzyme). Descriptions of the use of rationally-designed, multifunctional polymers, particularly for the purpose of cellular uptake and the subsequent release from intracellular vesicles, have not been described. To achieve the delivery of NPs into cells, a class of peptides known as cell penetrating peptides has been employed previously with success. These peptides, often based on the Tat-1 peptide of HIV, use the cells endocytic pathway to achieve the cellular uptake of the NPs. However, the NPs typically remain sequestered within the intracellular vesicles of the endocytic pathway and they must be physically or chemically induced to be released into the cell cytoplasm.

Described herein is a new approach for the functionalization of conceivably any NP with a rationally-designed, modular, multifunctional peptide to generate NP-peptide assemblies capable of "escaping" from within endocytic vesicles. The peptide carries out two main functions: (1) it mediates the cellular uptake of the NP to which it is attached and (2) it mediates the release of the NP-peptide assemblies from within intracellular endocytic vesicles. The peptide is comprised of separate functional domains that, while serving distinct roles. work together as an ensemble to impart multiple functionalities to the NP. In the example provided, the NP is a semiconductor quantum dot (QD) and the peptide is a multi-domain peptide that mediates the cellular binding, uptake, and subsequent intracellular dispersal of the QD.

Figure 7A:
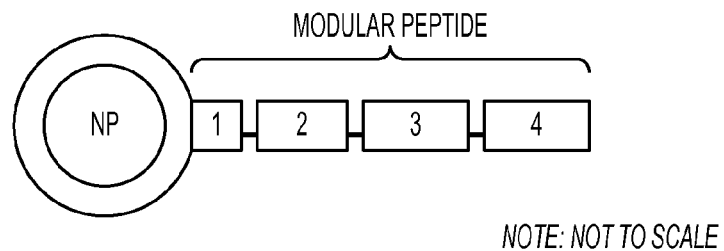
FIGS. 7A and 7B illustrate illustrates the functionalization of NPs with modular multifunctional peptides.

FIG. 7A shows a general schematic representation of an exemplary NP-peptide assembly, wherein the peptide comprises multiple functional domains: a NP association domain (1); a spacer domain (2): and multiple domains that impart biological activity (3 and 4). The multi-domain peptide interfaces with the NP surface via the peptide's NP-association domain. This association can be through either a covalent bond or a noncovalent interaction (e.g., electrostatic or metal ion coordination). Subsequent functional domains are located adjacent from the NP-association domain. Such peptides can be synthesized or they can be expressed and purified through molecular biology techniques known to a person of ordinary skill in the art.

Figure 7B:
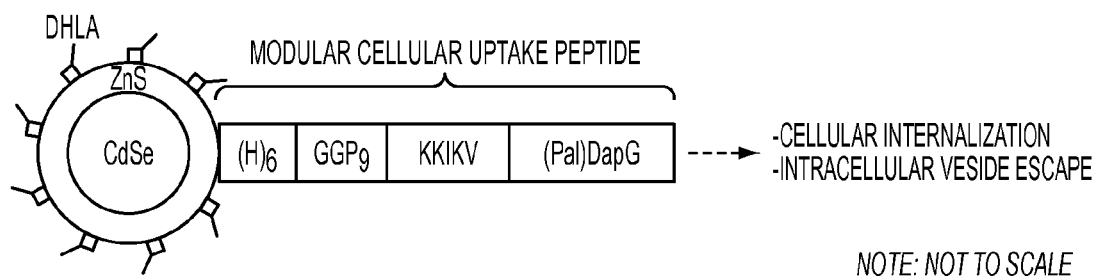

FIG. 7B shows an exemplary peptide attached to a QD and effective to provide for intracellular uptake and endosomal escape. The modular peptide consists of a 6-histidine (H6) domain for assembly to the QD surface, a proline-rich spacer domain (P9GG), a positively charged lysine-rich domain (VKIKK) for cellular association and uptake, and a synthetic palmitic acid group ((Pal) Dap, representing palmitoyldiamoniprionyl) for cell membrane association and insertion. The AcG(Pal)DapVKIKK portion of the sequence is derived from the C-terminus of the K-ras protein where the (Pal)Dap is a nonhydrolyzable mimic of a palmitoylated cyteine residue. This sequence has been shown to inhibit a palmitoyl thioesterase with low micromolar affinity in acidic environments. See G. Dawson et al., Biochemical and Biophysical Research Communications, 395 (2010) 66-69. It is believed that this protects the palmityl group from endosomal degradation. The domains act in concert to impart desirable biological capabilities to the QD. (Pal)Dap is sometimes referred to as Dap(Pal).

Numerous different multidomain, multifunctional peptides have been assembled to the surface of QDs. They can be monitored the intracellular fate of the different QD-peptide assemblies both in terms of the ability of the assemblies to be internalized by cells and to be liberated from with in intracellular vesicles (endosomes). To this end, three structurally similar, modular peptides were synthesized: Palm-1b, Palm-2b, and Palm-3b.

As compared to Palm-1 discussed above, the Palm-1b sequence lacks the terminal tryptophan which in Palm-1 serves to provide an aromatic ring structure for monitoring by absorption spectroscopy. It also uses N-acetylglycine in place of glycine. It is not believed that these differences result in any change in function with regard to ability to mediate delivery of nanoparticles.

The tested peptide sequences are shown below in Table 2. The three peptides share in common the hexa-histidine domain for assembly to a QD surface, the positively-charged lysine-rich domain (VKIKK) (SEQ ID No: 7) for cellular association and uptake, and a synthetic palmitic acid group ((Pal)Dap, representing palmitoyldiamoniprionyl) for cell membrane association and insertion. The three peptides differ, however. in the sequence of their spacer domains. The spacer domain of Palm-1 has two glycine residues followed by a nine proline repeat and is predicted to adopt a rigid, extended helical conformation based on the fixed side chain conformation of the successive pyrrolidine rings of the proline residues. The Palm-2b and Palm-3b peptides are glycine- and alanine-rich (with Palm-3b having one proline residue substituted for an alanine) and are expected to adopt shorter alpha-helical conformations relative to the proline helix.

TABLE 2

Multifunctional modular peptides for cellular uptake

| Peptide | Sequence | Sequence Number |
|---------|----------|-----------------|
| Palm-1b | AcG(Pal)DapVKIKK P$_9$GG H$_6$ | SEQ ID NO: 4 |
| Palm-2b | AcG(Pal)DapVKIKKGLAAAAGG H$_6$ | SEQ ID NO: 5 |
| Palm-3b | AcG(Pal)DapVKIKKGLAPAAGG H$_6$ | SEQ ID NO: 6 |

Pal, palmitoyl; Dap. diaminopropionic acid; Ac, acetyl group blocking the peptide's N-terminus.

Pal, palmitoyl; Dap. diaminopropionic acid; Ac, acetyl group blocking the peptide's N-terminus.

Palm-1b, Palm-2b, and Palm-3b have approximate molecular weights of 3992 Da, 3570 Da, and 3594 Da, respectively.

Figure 8:
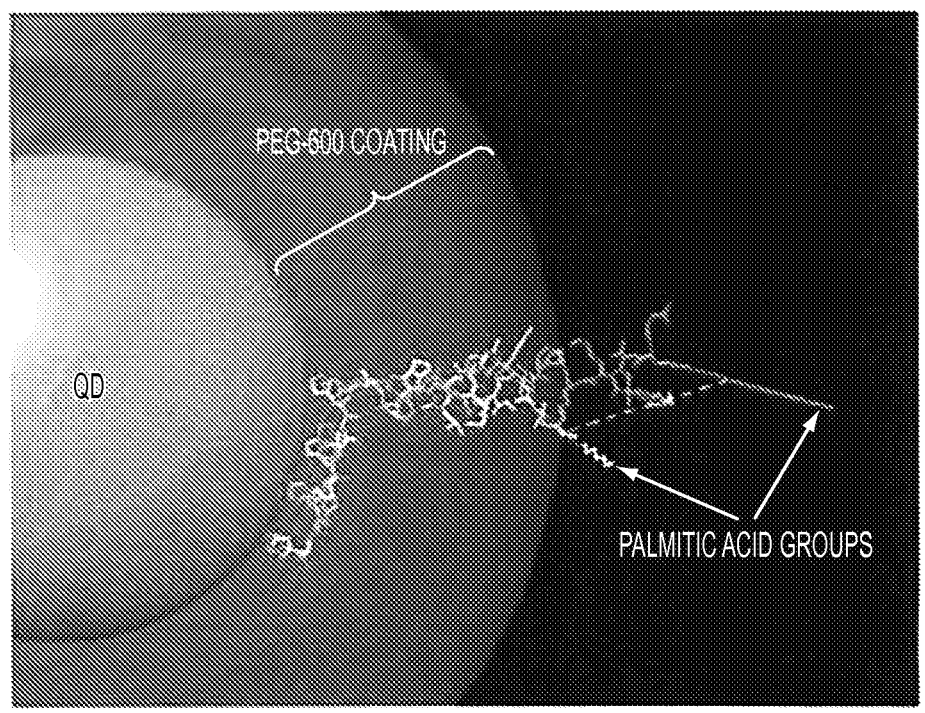
FIG. 8 illustrates a model of NP-peptide assemblies.

Molecular modeling was employed to examine the effects of the different spacer domain sequences on the conformation of the peptides within the QD-peptide assemblies, as seen in FIG. 8, which shows the resulting overlaid QD-peptide models obtained when each peptide was energy minimized for its association with the QD surface via its 6-histidine domain. Shown is are comparative models of each of three Palm peptides assembled onto the surface of a QD bearing a polyethylene glycol-600 (PEG-600) surface coating. The Palm-1b peptide is shown in medium-gray while the Palm-2b and Palm-3b peptides arc shown in white and dark gray, respectively. Each peptide is shown assembled with the QD surface shell via its 6-histidine domain. The spacer domains of the Palm-2b and Pal-3b peptides adopt a short alpha-helical conformation that allows only a portion of the lysine-rich domain and the palmitic acid group to protrude from the PEG-600 layer. The proline repeat-containing spacer of Palm-1, however, adopts a rigid, more extended helical conformation that positions both the lysine-rich cell-binding domain and the palmitic acid group well beyond the PEG layer, making them readily accessible to the cell surface. The spacer extends about ~30 Å through the PEG-600 layer and presents the lysine-rich cell-binding domain and the palmitic acid group in an accessible orientation beyond the PEG layer. The extended spacer domain of Palm-1b positions the palmitic acid group approximately 22 Å further away from the PEG layer relative to the Palm-2b and Palm-3b peptides.

Figure 9A:
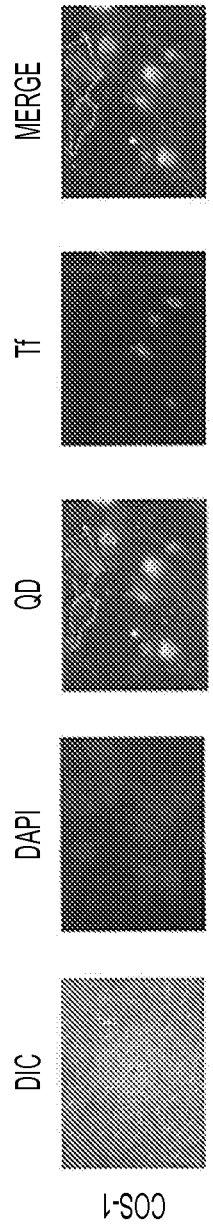
FIGS. 9A-9C illustrate illustrates the cellular uptake and intracellular fate of various QD-peptide assemblies.
Figure 9B:
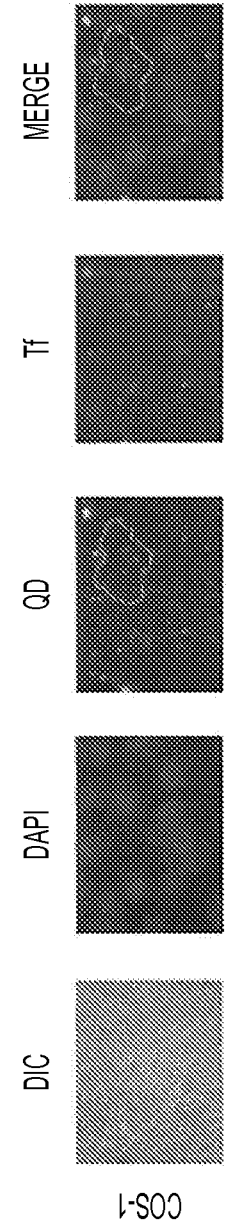
Figure 9C:
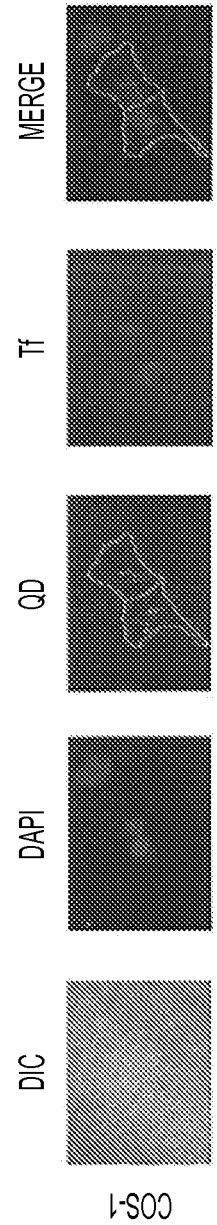

The functional implications of the different conformations of the Palm peptides with in the QD-peptide assemblies were assessed by cell delivery experiments, as seen in FIG. 9. In FIGS. 9A, B, and C, the assembles have Palm-1b, Palm-2b, and Palm-3b, respectively.

The peptide assemblies were incubated with COS-1 cells for 1 hr, removed, and the cells were subsequently cultured for 24 hr prior to fixation. An AlexaFluor 647-transferrin (Tf) conjugate was included during the incubation to label the vesicles of the endocytic pathway. Cell nuclei were stained with DAPI. Upon internalization, the Palm-1b QD-peptide assemblies were largely well dispersed throughout the cytoplasm and were not colocalized with the endocytic marker. The Palm-2b and Palm-3b QD assemblies were nearly entirely sequestered within endosomes.

The intracellular fate of the three different QD-peptide assemblies was monitored after incubation with COS-1 cells by noting the distribution of the assemblies within the cell and by labeling the endocytic pathway with a marker specific for endosomes (AlexaFluor 647-conjugated transferrin). As shown in FIG. 9, each of the three peptides mediated intracellular uptake of the QD-peptide assemblies. A notable difference was observed in the intracellular distribution of the assemblies. The Palm-2b and Palm-3b assemblies remained completely sequestered within endocytic vesicles as evidenced by their colocalization with the endosomal marker. The Palm-1b QD-peptide assemblies, however, were well-dispersed throughout the cytoplasm while only a small percentage was colocalized within endosomes. Thus, the proline-rich spacer domain of Palm-1b in conjunction with the other modular peptide properties combine to mediate both cellular uptake and endosomal escape of the QD-peptide assemblies.

Domains of a Peptide for Delivery of Nanoparticles.

A peptide for delivery of a nanoparticle to the cytosol comprises: (a) a nanoparticle association domain; (b) a spacer domain; (c) an uptake domain; and (d) a vesicle escape domain comprising a non-hydrolyzable lipid moiety.

One of ordinary skill in the art may configure the nanoparticle association domain to make the peptide amenable to either covalent and noncovalent attachment strategies. For example, the nanoparticle association domain can be a polyhistidine sequence which noncovalently binds metal in a payload, such as a metallic quantum dot. A polyhistidine domain could also be used to bind a nickel-nitrilotriacetic acid (Ni-NTA) linker, where the linker can be attached to a payload such as a drug. The nanoparticle association domain could also be adapted for coupling to a payload using 1-ethyl-3-[3-dimethylaminopropyl]carbodiimide hydrochloride (EDC) for crosslinking a carboxyl groups to a primary amine. Other possible conjugation protocols for the nanoparticle association domain are known to one of ordinary skill in the art, and include maleimide dithiol exchange, diazonium salt chemistry, and the like. In another embodiment, the nanoparticle association domain comprises a plurality of either positively- or negatively-charged amino acid residues, so that the peptide is electrostatically attracted to a payload having an opposing charge.

The spacer domain serves to reduce to reduce steric hindrance between the peptide and the surface of the nanoparticle, and may have other functions. Optionally, the spacer has a length 6, 7, 8, 9, 10, 11, 12, 13, 14, or 15 proline residues. In an embodiment, the spacer comprises a poly-proline repeat. In another embodiment, the spacer comprises a poly-arginine repeat. In yet another embodiment, the spacer comprises a number of synthetic peptides, such as Aib (alpha-amino isobutyric acid).

The uptake domain is preferably a positively charged lysine-rich domain such as VKIKK (SEQ ID No: 7).

The vesicle escape domain preferably comprises a non-hydrolyzable lipid moiety. Such a lipid moiety includes at least eight carbons. Optionally, there may be more than one such moiety, for example diamoniproprionyl-glycine-diamoniproprionyl. In one embodiment, the lipid moiety is palmitate (palmitic acid). One of ordinary skill in the art would recognize that another lipid moeity might be used to obtain the desired cell membrane association, insertion, and/or vesicle escape. Such moieties include octanoic, 2-ethylhexanoic, nonanoic, decanoic, lauric, myristic, margaric, stearic, arachidic, behenic, lignoceric acid or unsaturated monocarboxylic acids such as oleic, linoleic, linolenic, ricinoleic acid or aromatic monocarboxylic acids such as benzoic acid, aliphatic dicarboxylic or polycarboxylic acids such as succinic, glutaric, adipic, pimelic, suberic, azelaic, sebacic, nonanedicarboxylic, decanedicarboxylic, dimer fatty acids, which are obtainable by dimerizing unsaturated monocarboxylic acids; aromatic dicarboxylic or polycarboxylic acids such as terephthalic, isophthalic, o-phthalic, tetrahydrophthalic, hexahydrophthalic or trimellitic acid, for example. Other such moieties include cholesterol. Also included in the definition of lipid moeity as used herein are perfluorocarbon-containing compounds having at least eight carbons. Most preferable, the lipid moiety is non-hydrolyzable.

Modular design of functional domains allows for flexibility in iterative peptide development and testing. Further experiments were conducted to investigate the roles of these domains. The tested peptides (including controls) and the results of the experiments are shown in Table 3.

TABLE 3

Additional Peptides Tested

| Peptide | Sequence | Description | SEQ ID No: |
|---|---|---|---|
| JB577 (Palm-1) | WGDap$_a$VKIKK(P)9GG(H)6 | Endosomal escape peptide | 2 |
| Palm 2 | WGDap$_a$VKIKKGL(A)4GG(H)6 | No (Pro)9, short linker | 9 |
| Palm 3 | WGDap$_a$VKIKKGLPAAGG(H)6 | No (Pro)9, shorter linker | 10 |
| JB582 | WGDap$_a$VKIKK(P)4GG(H)6 | Shorter (Pro)4 linker | 11 |
| JB747 | WGDap$_a$VKIKK(Aib)9GG(H)6 | (Pro)9 replaced with (Aib)9 | 12 |
| JB865 | WGDap$_a$VKIKK(P)12GG(H)6 | Longer (Pro)12 linker | 13 |
| JB864 | WGDap$_a$VKIKK(P)15GG(H)6 | Longer (Pro)15 linker | 14 |
| JB578 | WGDap$_a$(P)9GG(H)6 | No Lysine residues (uncharged) | 15 |
| JB583 | WGDap$_a$VRRRIRR(P)9GG(H)6 | Arg substituted for Lys | 16 |

TABLE 3-continued Additional Peptides Tested

| Peptide | Sequence | Description | SEQ ID No: |
|---|---|---|---|
| JB585 | WGDapVRRRIRR(P)9GG(H)6 | Arg substituted for Lys, no palmitate | 17 |
| JB833 | WGDap$_a$AGAGG(A)4Aib(A)4GG(H)6 | Uncharged Palm-only | 18 |
| JB869 | WGDap$_a$VRL(P)3VRL(P)3VRL(P)3GG(H)6 | Amphipathic repeat places VKIKK(P)9 | 19 |
| JB868 | WGDapVRL(P)3VRL(P)3VRL(P)3GG(H)6 | Amphipathic VRL(P)3 3-repeat; no palmitate | 20 |
| JB579 | WGDapVKIKK(P)9GG(H)6 | No palmitate group | 21 |
| JB580 | WGDap$_a$GDapaVKIKK(P)9GG(H)6 | Two palmitates | 22 |
| JB866 | WGDap$_{aa}$VKIKK(P)9GG(H)6 | Two palmitates on Dap | 23 |
| JB589 | WGCcVKIKK(P)9GG(H)6 | Hydrolyzable palmitate | 24 |
| JB858 | WGDab$_a$VKIKK(P)9GG(H)6 | Dab replaces Dap | 25 |
| JB641 | WGDap$_{di}$VKIKK(P)9GG(H)6 | 8-carbon alkane group (ontanoyl) substituted for palmitate | 26 |
| JB621 | W$_d$GDap$_{di}$VKIKK(P)9GG(H)6 | Two octanoyl groups | 27 |
| JB729 | WGDap$_e$VKIKK(P)9GG(H)6 | Highly-fluorinated group substituted for palmitate | 28 |
| SI-09160 | WGDap$_j$VKIKK(P)9GG(H)6 | Cholesterol substituted for palmitate | 29 |
| JB876 | WGC$_{fx}$VKIKK(P)9GG(H)6 | Modified cholesterol on cys | 30 |
| JB872 | WGC$_g$VKIKK(P)9GG(H)6 | Farnesyl replaces Palmitate | 31 |
| JB859 | (H)6GG(P)9WGDap$_a$VKIKK | Reversed sequence 1 | 32 |
| JB860 | (H)6GG(P)9VKIKKDap$_a$GW | Reversed sequence 2 | 33 |
| JB862 | VKIKKWGDap$_a$(P)9GG(H)6 | Reversed sequence 3 | 34 |
| JB588 | WGDap$_a$RRRIRR(P)9GGK | No (His)6, for EDC coupling | 35 |
| JB728 | WGDap$_a$VKIKK(P)9GGK$_b$ | Dye-labeled Enx1 | 36 |
| JB722 | $_{bi}$KWGSAibAAALGG(R)10 | Dye labeled cell penetrating peptide | 37 |
| JB719 | KETWWETWWTEWSQPKKKRKVSGAibAAAGG(H)6 | Chariot peptide | 38 |
| JB532 | C(P)9GG(H)6 | Texas-Red (Pro)9 peptide (FRET acceptor) | 39 |
| JB434 | (R)9GGLAAibSGWK(H)6 | cell penetrating peptide | 40 |
| JB867 | K$_h$GDap$_a$VKIKK(P)9GG(H)6 | Enx1 w/N-terminal TAMRA | 41 |

Figure 10:
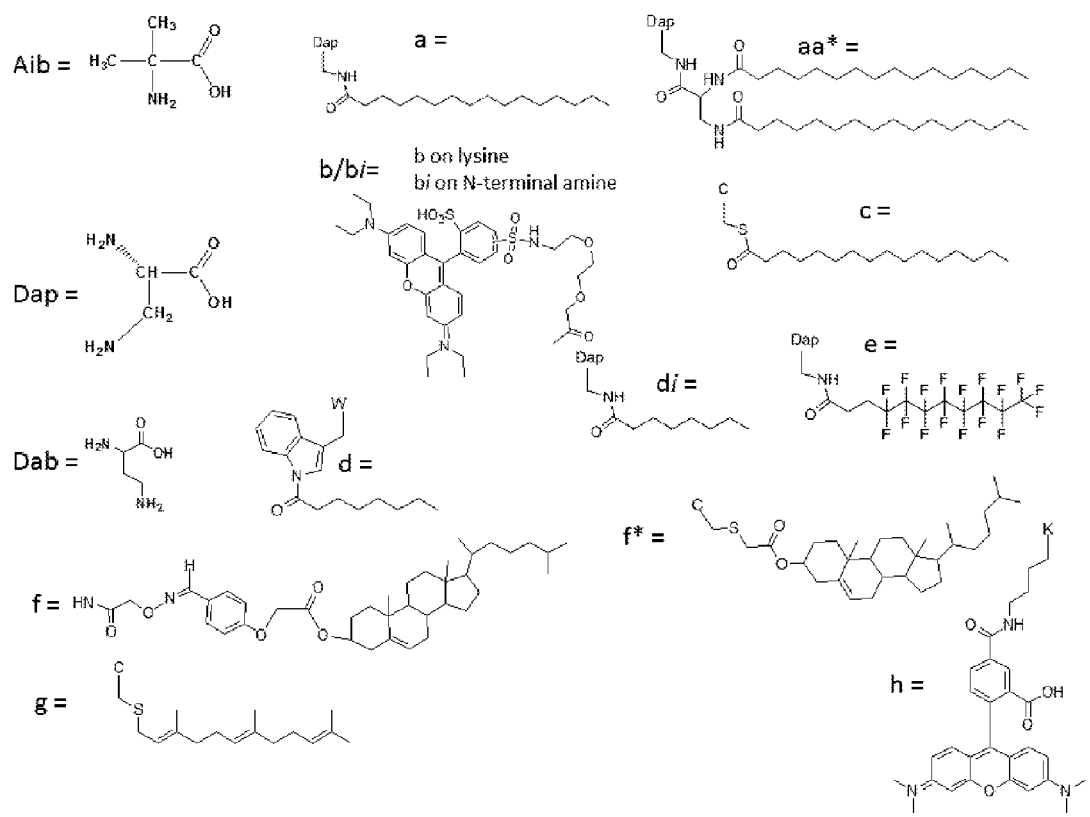
FIG. 10 illustrates various moieties employed in the peptides described herein. "Dab" represents diaminobutyric acid.

In Table 3, "Dap" represents 2,3-Diaminopropionic acid, which is also called "Dpr." "Dab" represents diaminobutyric acid. "Aib" refers to alpha-amino isobutyric acid. Subscripts within the sequences refer to the moieties depicted in FIG. 10.

Results of tests of update and endosomal escape of these peptides in COS1 cells are provided in Table 4.

TABLE 4

Results of Tests on Additional Peptides

| Peptide (description) | # of cells (n) | % QD uptake (n) | % endosomal escape of total cells (n) | % Escape in cells with uptake | Overall uptake/escape[1] |
|---|---|---|---|---|---|
| JB577 (Palm-1) | 76 | 92% (70) | 69% (52) | 77% | High/high |
| JB578 (Palm-1 uncharged) | 159 | 8% (13) | 4% (6) | 46% | Low/moderate |
| JB579 (Palm-minus) | 82 | 17% (14) | 5% (4) | 29% | Low/low |
| JB580 (Palm-1 X2) | 90 | 13% (12) | 12% (11) | 92% | Low/high |
| JB582 (Palm-1/4 Pro) | 67 | 0% (0) | 0% (0) | n/a | None/none |
| JB583 (Palm-1/R for K) | 155 | 19% (29) | 8% (12) | 41% | Low/moderate |
| JB585 (Palm-minus/R for K) | 199 | 2% (4) | 0.5% (1) | 25% | Low/low |
| JB589 (Palm-1/hydrolyzable) | 144 | 6% (8) | 3% (4) | 50% | Low/moderate |
| JB833 (uncharged with Palm) | — | Not available | — | — | — |
| JB858 (Dab for Dap) | — | Membrane localized | — | — | — |
| JB859 (Reverse order, palm before VKIKK) | 180 | 57% (103) | 10% (19) | 17% | Moderate/low |
| JB862 (VKIKK moved) | 163 | 21% (35) | 3% (3) | 9% | Low/low |
| JB866 (2 Palm groups on Dap) | 197 | 45% (89) | 5% (10) | 11% | Moderate/low |
| JB621 (Octanoyl X2) | 241 | 29% (69) | 26% (62) | 90% | Low/high |
| JB641 (Octanoyl) | 165 | 50% (83) | 44% (73) | 88% | Moderate/high |
| JB747 (Palm-1/Aib for P) | 78 | 100% (78) | 58% (45) | 58% | High/moderate |
| JB729 (Palm-minus/fluorine) | 80 | 64% (51) | 54% (43) | 84% | High/high |
| SI09160 (Palm-minus/cholesterol) | 102 | 44% (45) | 42% (43) | 96% | Moderate/high |
| JB860 (Reverse order) | 164 | 30% (50) | 18% (30) | 60% | Moderate/moderate |
| JB865 (P12 for P9) | 82 | 80% (66) | 85% (56) | 68% | High/moderate |
| JB864 (P15 for P9) | 99 | 82% (81) | 70% (69) | 85% | High/high |
| JB872 (Palm-minus/farnesyl) | 101 | 99% (100) | 78% (79) | 79% | High/high |
| JB869 (3 Amphipathic VRLPs for P) | 315 | 80% (253) | 44% (139) | 55% | High/moderate |
| JB868 (3 Amphipathic VRLPs for P, no palm) | 171 | 59% (101) | 11% (19) | 18% | Moderate/low |
| JB876 (Cholesterol for palm, Cys linkage) | — | Not available | | | |
| JB867 (Palm/TAM - integrity) | | >90% QD/TAMRA colocalized | | | |
| JB588 (EDC conjugated) | 64 | 94% (60) | 80% (51) | 85% | High/high |
| JB728 (Palm-1 Rhodamine) | 84 | 81% (68) | 76% (63) | 93% | High/high |
| JB719 (Chariot peptide) | 180 | 53% (96) | 23% (41) | 43% | Moderate/moderate |
| JB722 (CPP Rhodamine) | 94 | 13% (12) | 8% (1) | 1% | Low/low |

The Palm-1 peptide was also tested in HeLa cells, and found to be very effective in promoting endosomal escape. From a collection of 163 HeLa cells administered Palm-1 conjugated to a quantum dot (QD), 90% (147) demonstrated QD uptake, 77% (126) of the total demonstrated endosomal escape, so that 86% of the cells with uptake demonstrated endosomal escape.

As a further example, a peptide having the described domains was successful in delivering the 240-kDa B-phycoerythrin protein to the cellular cytosol.

The described peptides could be expressed using recombinant technology, optionally together with one or more additional peptide or protein domains to provide further functionality. Such functionality can include therapeutic functions. For example, one of ordinary skill could design an expression vector for transient and/or stable expression in a cell, tissue, or organism of a protein incorporating one or more of the described peptides.

The strategy described herein is amenable to the assembly of a wide range of nanoparticles with a modular, multifunctional peptide. The NP surface can be functionalized with different types of modular, multifunctional peptides ("mixed" surfaces), giving ratiometric control over the nature of the decorated NP surface. Specifically for cell penetrating peptide-mediated NP uptake, a peptide sequence that can either individually or cumulatively: inherently interact with/attach itself to the NP surface; is amenable to having its lateral extension or rigidity controllably adjusted; contains a cell-penetrating domain; contains an endocytic vesicle escape sequence; potential to express or contain other modular functional domains as desired; and the ratio or valence (and thus the avidity) on the NP can be controlled.

Described herein are peptides that include multiple overlapping functional domains, the combination of which contributes to both endocytosis and subsequent release to the cytosol of either the peptide itself or the peptide attached to a nanoscale payload. Such payloads include proteins, carbohydrates, and other biological materials, drugs, contrast agents (or other imaging agents), nucleic acids, and/or gene therapy agents.

As described above, CdSe/ZnS core/shell luminescent semiconductor nanocrystals or "quantum dots" (QDs) coated with polyethylene glycol (PEG)-appended dihydrolipoic acid (DHLA) can bind certain peptides incorporating the histidine residues. The coating on the QD provides colloidal stability and the peptide complex allows the QDs to be taken up by cultured cells and readily exit the endosome into the soma.

In order to extend the usefulness of QDs, the coating and peptide:QD ratio were varied and tested for cell-type specificity and subcellular distribution in a differentiating rat hippocampal slice culture system. Previous studies using QDs have largely failed to show selective cell targeting, although two recent studies have shown selective targeting of streptavidin coated QDs to microglia (Minami, et al. 2012) and atheronol-B analog coated QDs to macrophages (Prapainop, et al. 2012). There was also a report that nanoparticles coated with polysorbate 80 could transport an analgesic peptide across the blood brain barrier after intranasal administration (Ruan, et al. 2012). Here, it was desired to target the QD-peptide to neurons while minimizing distribution elsewhere, using a hippocampal slice culture model system.

Figure 11:
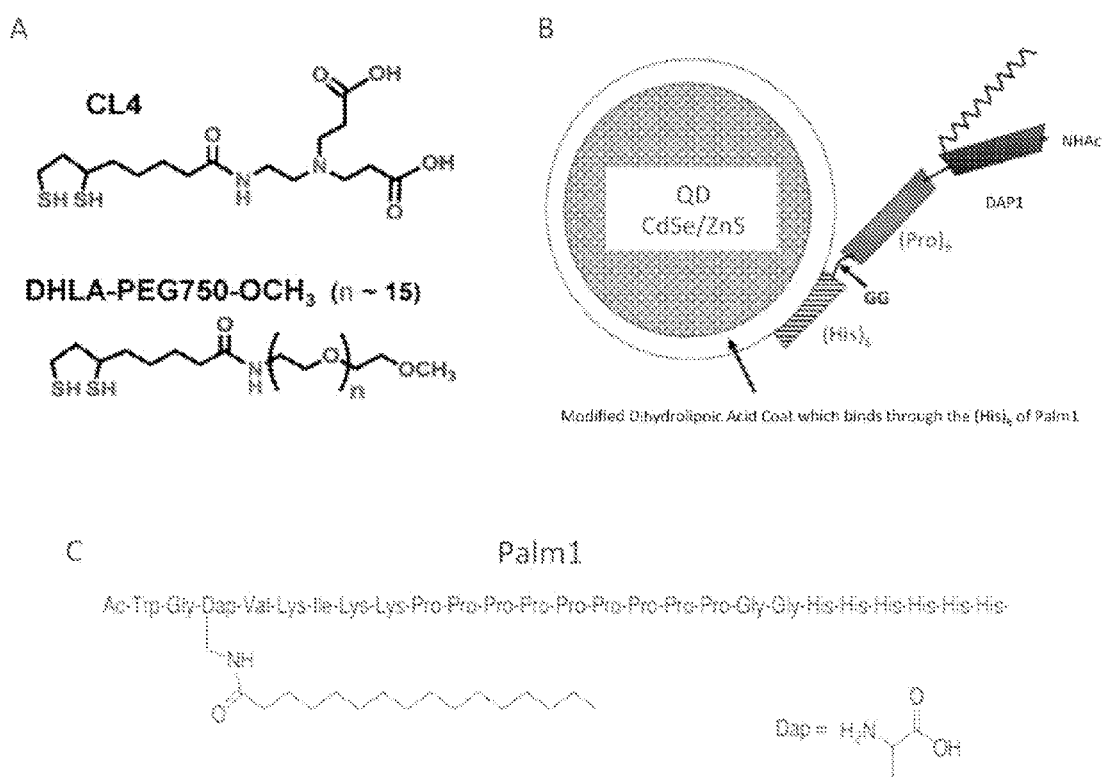
FIGS. 11A and 11B depicts various structures.
FIG. 11C shows the structure of Palm1 peptide.

The use of a polyampholyte coating, in which the neutral PEG is replaced by the negatively heterocharged compact ligand, ("CL4"), resulted in the specific targeting of the palmitoylated peptide to neurons in mature rat hippocampal slice cultures without noticeable uptake by astrocytes, oligodendrocytes, or microglia, with endosomal egress via the Palm1 peptide, suggesting a novel and robust way of delivering neurotherapeutics to neurons. FIG. 11A shows the structure of CL4 (above) shown in relation to a PEG ligand (below). FIG. 11B is a schematic of Palm1 peptide conjugated to a QD via histidine binding to the ZnS surface. FIG. 11C shows the structure of Palm1 peptide.

Experimental Details

Quantum Dots

CdSe—ZnS core-shell QDs with emission maxima centered at 635 nm were synthesized (Invitrogen) and made hydrophilic by exchanging the native trioctylphosphine/trioctylphosphine oxide (TOP/TOPO) capping shell with dihydrolipoic acid (DHLA)-based ligands. For peptide-mediated delivery, neutral polyethylene glycol (PEG)-appended DHLA ligands were attached as described previously (Susumu, et al. 2007; Mei, et al. 2008). For cell specific delivery the more compact, negatively charged polyampholyte CL4 was used.

Peptides.

The palmitoylated peptide (Palm1) sequence used was WG(Pal)VKIKKP9GGH6 where 'Pal' corresponds to a palmitate group that is covalently attached to a non-hydrolyzable thiol-resembling diaminopropionic acid residue functionality synthesized into the peptide backbone (Sapsford, et al. 2007). All peptides were synthesized using Boc-solid phase peptide synthesis, purified by HPLC, and purity verified by electrospray ionization mass spectrometry (Dawson et al., 2010). All peptide sequences are written in the conventional amino-to-carboxy terminus orientation.

Peptide-Mediated Delivery.

QD-Palm1 bioconjugates were formed by diluting a stock solution of preformed peptide-QD complexes (1 µM QD assembled with 12.5, 25 or 75 Palm1 peptides per QD in 0.1 M borate buffer, pH 8.9) into complete growth medium to a final QD concentration of 50-100 nM. These peptide:QD ratios were determined experimentally for the peptide to be the ratio that yielded the optimal degree of uptake. The self-assembled bioconjugates were then incubated with cells as described below.

Uptake by Rat Hippocampal Slice Cultures.

Hippocampal cultures were prepared as described previously (Kunkler and Kraig 1997; Mitchell, et al. 2010). Briefly, Wistar rat pups (P9-P10) were anesthetized with a progressive exposure to 100% carbon dioxide and decapitated, the brains removed and placed into HBSS (3° C.) supplemented with D-glucose (6.5 mg/ml). Hippocampi were then isolated and sectioned (350 µm thick) perpendicular to their septotemporal axis. Slices displaying an intact pyramidal neuron cell layer and dentate gyms were transferred to uncoated 30 mm Millicell-CM™ tissue culture inserts (Millipore, Bedford, Mass.) in six-well culture dishes. Cultures were initially maintained in media containing 23% horse serum (#26050-088; Invitrogen, Carlsbad, Calif., USA) for 18d in vitro before being transferred to serum-free media for an additional 3d in vitro before experimentation (Mitchell, et al. 2010). Slice cultures were used between 21-35d in vitro. The constituents of horse serum-based media and serum-free media are defined elsewhere (Mitchell, et al. 2010).

Hippocampal brain slice cultures mature in vitro and closely resemble the anatomical and physiological characteristics of their in vivo counterpart (e.g., see (Kunkler and Kraig 1997; Kunkler and Kraig 1998; Hulse, et al. 2004; Kunkler and Kraig 2004; Kunkler, et al. 2005; Grinberg, et al. 2011; Pusic, et al. 2011; Grinberg, et al. 2012)

Antibodies and Staining.

Hippocampal slices were fixed to gel coated slides using Prolong Gold Antifade (Invitrogen, #P36931) containing 4',6-diamidino-2-phenylindole (DAPI), a nuclear stain which binds strongly to A-T rich regions in DNA. Neuronal staining was carried out through Nissl staining with NeuroTrace 500/525 green (Invitrogen, #N21480) which binds to negatively charged nucleic acids in the endoplasmic reticulum of neurons (Quinn, et al. 1995). Cell viability was assessed by Sytox staining, identifying the neurons a monoclonal RIP antibody (Millipore, #MAB1580) which has been shown to specifically recognize 2',3'-cyclic nucleotide 3'-phosphodiesterase in oligodendrocytes (Watanabe, et al. 2006). To stain for astrocytes, a monoclonal antibody to glial fibrillary acidic protein (GFAP, Sigma, #G3893), largely expressed in astrocytes was employed, and shown to be a robust method of detection (Courel, et al. 1986). Microglia were stained using isolectin b4 (Invitrogen, #I21411), isolated from the African legume *Griffonia simplicifolia*, shown to be a robust stain for microglia (Streit 1990).

Microscopy and Image Analysis.

The intracellular distribution of QDs was analyzed by fluorescence microscopy using a Marianas fully automated Yokogawa type spinning disk confocal microscope equipped with ×40 and ×100 oil immersion lenses.

Electron Microscopy.

Figure 12:
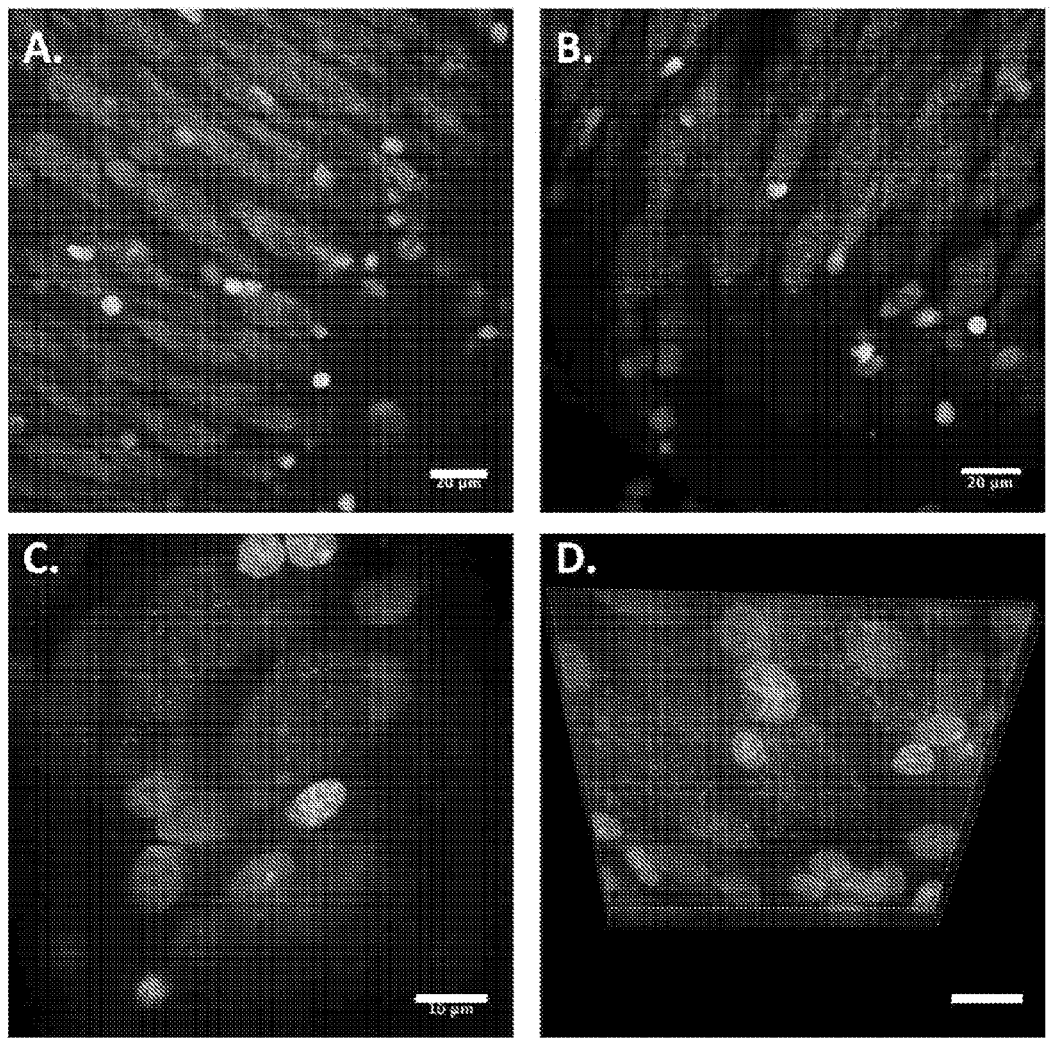
FIG. 12 shows confocal images of cell uptake of the CL4 QD-Palm1 complex.
Figure 13:
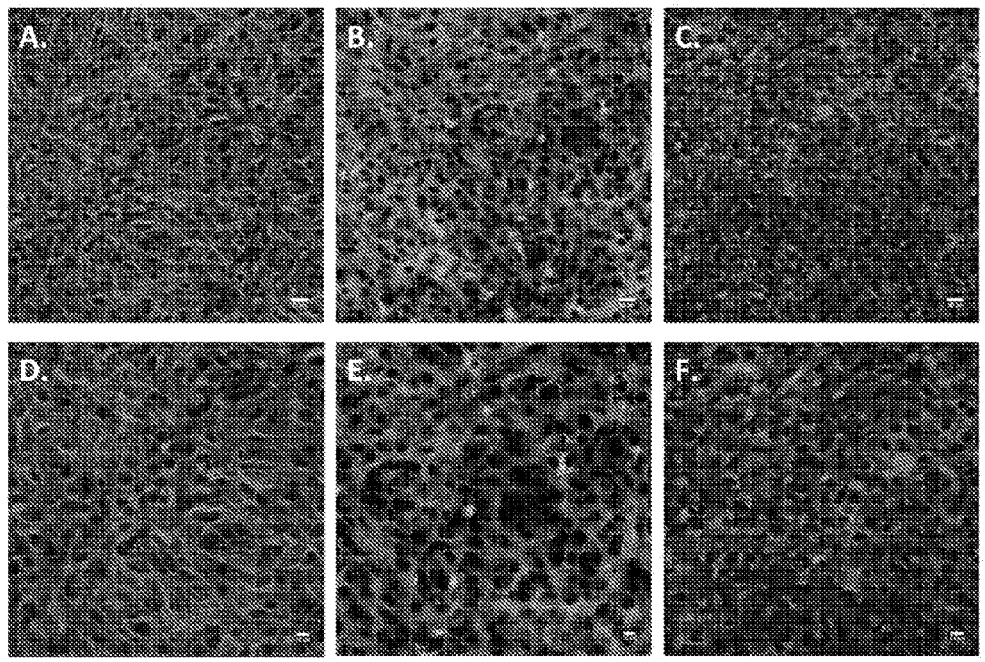
FIGS. 13A through 13F show confocal images demonstating that the CL4 QD-Palm1 complex is neuron specific. Cell-specific staining (green) was employed to determine if the QDs (red) were distributing to other common organelles found in our slice culture system and found no trafficking to astrocytes (FIGS. 13 A and 13D), microglia (FIGS. 13B and 13E) or oligodendrocytes (FIGS. 13C and 13F). This confirms that the QD-Palm1 complex targets neurons specifically in a complex in vitro system. Scale bars in FIGS. 13A-C are 20 µm and in FIGS. 13D-F are 10 µm
Figure 14:
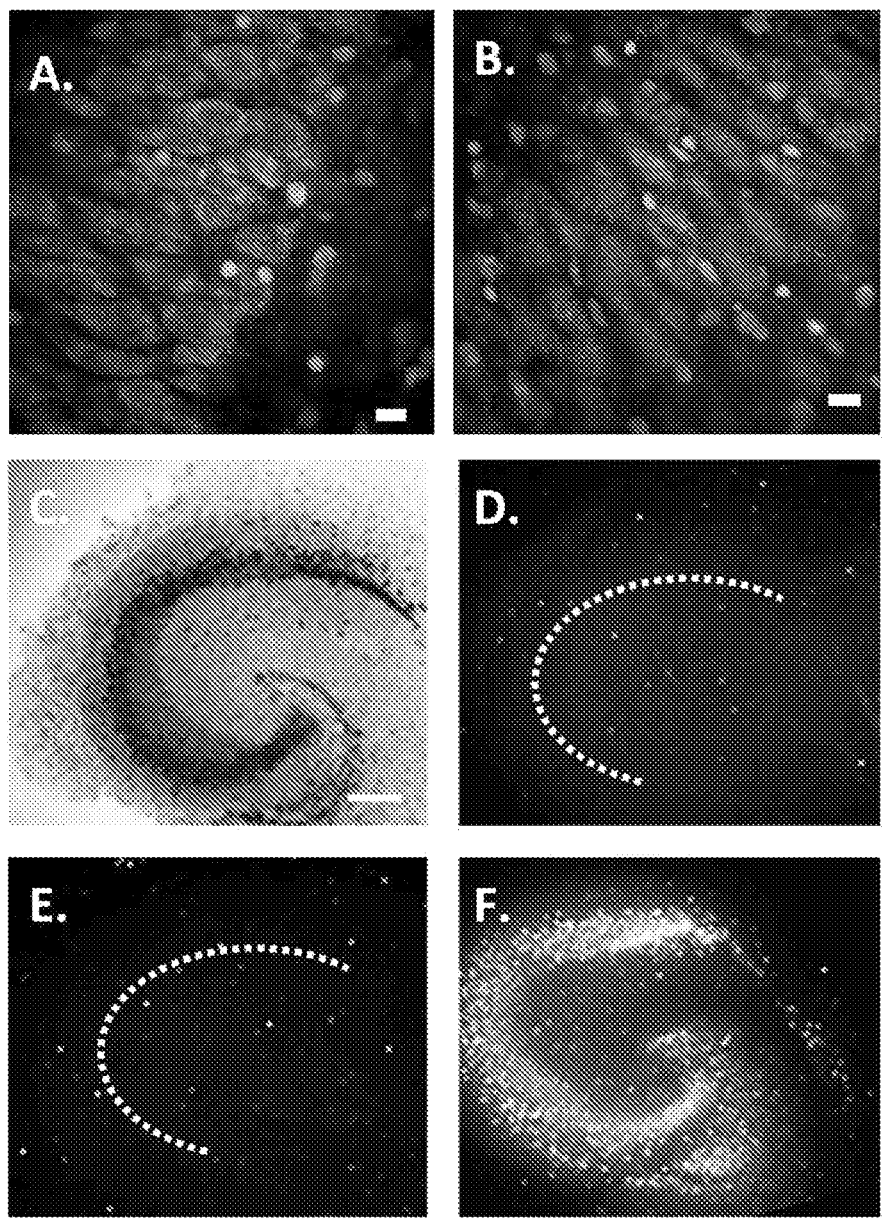
FIGS. 14A through 14F shows CL4 QD-Palm1 (red) after 48 h (FIG. 14A) and 72 h (FIG. 14B) in culture (Nissl is green, DAPI is blue).

All EM (electron microscopy) pictures were prepared and imaged at the University of Chicago electron microscopy core. Samples were fixed with 2% glutaraldehyde and 4% paraformaldehyde in 0.1M sodium cacodylate buffer for 2 h and then washed with sodium cacodylate buffer 3× for 5 m. Samples were post fixed for 60 m in 1% Osmium Tetroxide in 0.1M sodium cacodylate buffer. Samples were then polymerized with Polymerize Spurr and placed in 60° C. for 1-2d. 90 nm sections were cut by Reichert-Jung Ultracut E. and stained with uranyl acetate and lead citrate. All images were Results 1. Selective Targeting to Neurons in Hippocampal Slice Culture Researchers administered 10-12 μl of colloidal QD-peptide conjugate to 1.2 mL media of hippocampal slice cultures (final concentration of 50-100 nM) and incubated at 36° C. for 24 h. Afterwards, slices were fixed and prepared for imaging as described above. After 24 h in culture, CL4 coated QD-peptide conjugates showed patterns of distribution primarily within neurons along the CA3 cell layer (FIG. 12). In contrast, the CL4 coated QD-peptide conjugates provided little to no delivery to GFAP-positive astrocytes, isolectin-positive microglia, or CNPase-positive oligodendrocytes (FIG. 13). Additionally, we observed no QD-induced cytotoxicity in the cultures after 72 h of CL4-Palm1 exposure and staining with Sytox (FIG. 4). Neurons were identified by morphology and NeuN staining. This is in agreement with Minami et al. (2012), who observed no cytotoxic effects after direct injection into the mouse hippocampus for up to 28d (Minami, et al. 2012).

Figure 15:
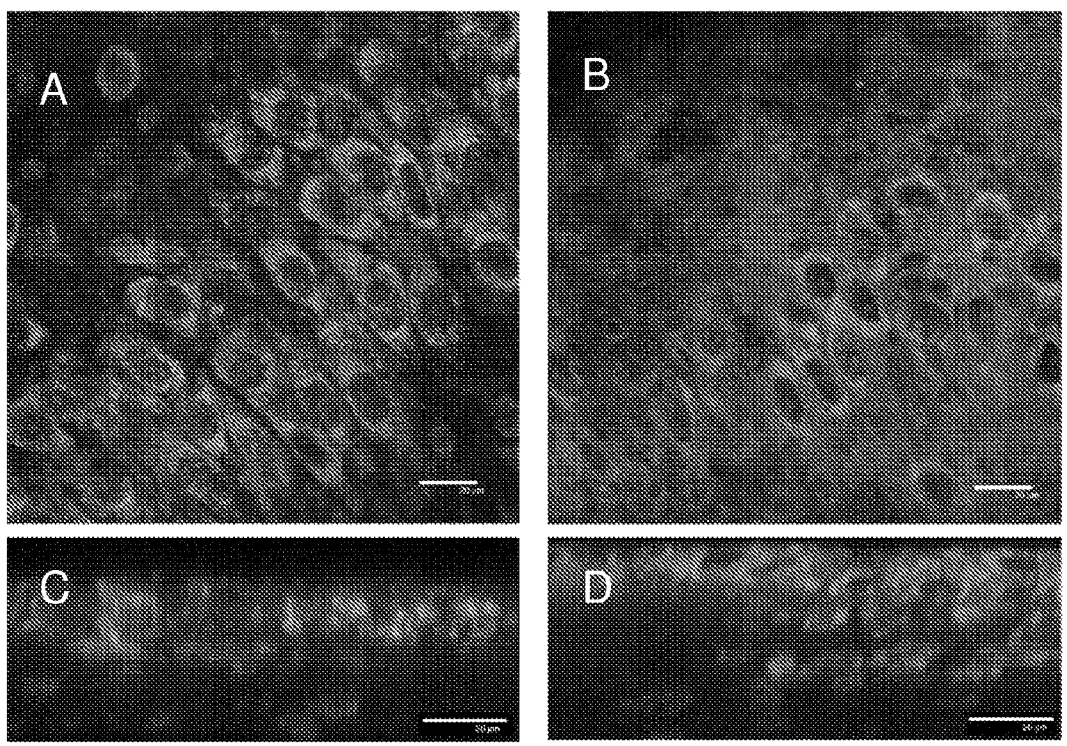
FIGS. 15A through 15D show that CL4 alone mediates intracellular uptake. Confocal images of CL4 QDs (FIG. 15A) or PEG QDs (FIGS. 15B-D) without peptide.

Other CL4-coated QDs, lacking the Palm1 peptide, showed the same neuronal specificity as those described above (FIG. 15A). This was in marked contrast to QDs coated with PEG, also without the Palm1 peptide, which failed to show either specific cell-type targeting or cell uptake (FIGS. 15B-15D). Surprisingly, the CL4 coat alone confers unique neuronal targeting properties to these QDs with no need for a targeting peptide in the in vitro slice model. This provides researchers with additional variables for tuning the QD-peptide delivery system to target cells of interest, possibly in a variety of disease models and applications. However, the lack of the Palm-1 means that the QDs do not readily egress into other subcelluar compartments.

2. Quantum Dot Delivery was not Impeded by Slice Culture Thickness or Application Method.

Figure 16:
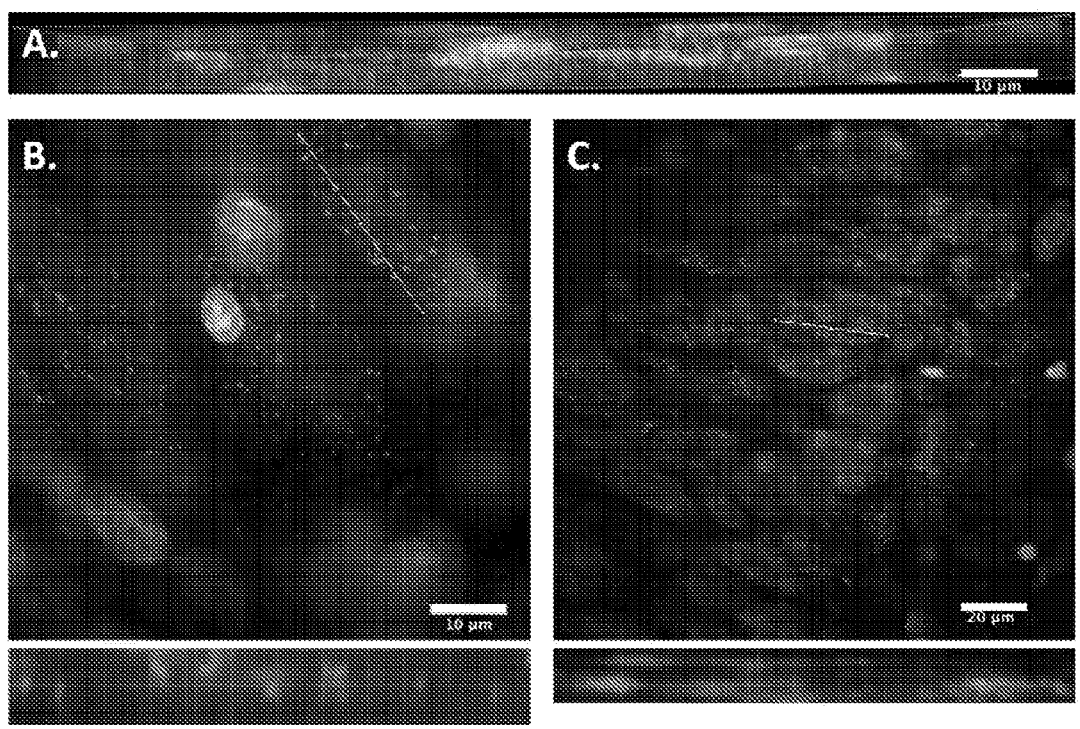
FIGS. 16A through 16C show slice penetration of CL4 QD complex.

In the brain slice culture system employed herein, hippocampal slices sit upon a membrane suspended above culture media. The QDs are applied directly to the media and allowed to naturally diffuse into the tissue from the bottom up. To eliminate concerns that the QDs might not distribute past the surface of the tissue, we a series of z-stacks were compiled that showed that the CL4 QDs did penetrate the surface and were distributed throughout the tissue (FIG. 16A). Additionally, z-stack images also show that the QDs penetrated through the cell membrane to the intracellular milieu, as opposed to merely sticking to the surface of the soma (FIGS. 16B and 16C).

3. Endosomal Release

Figure 17:
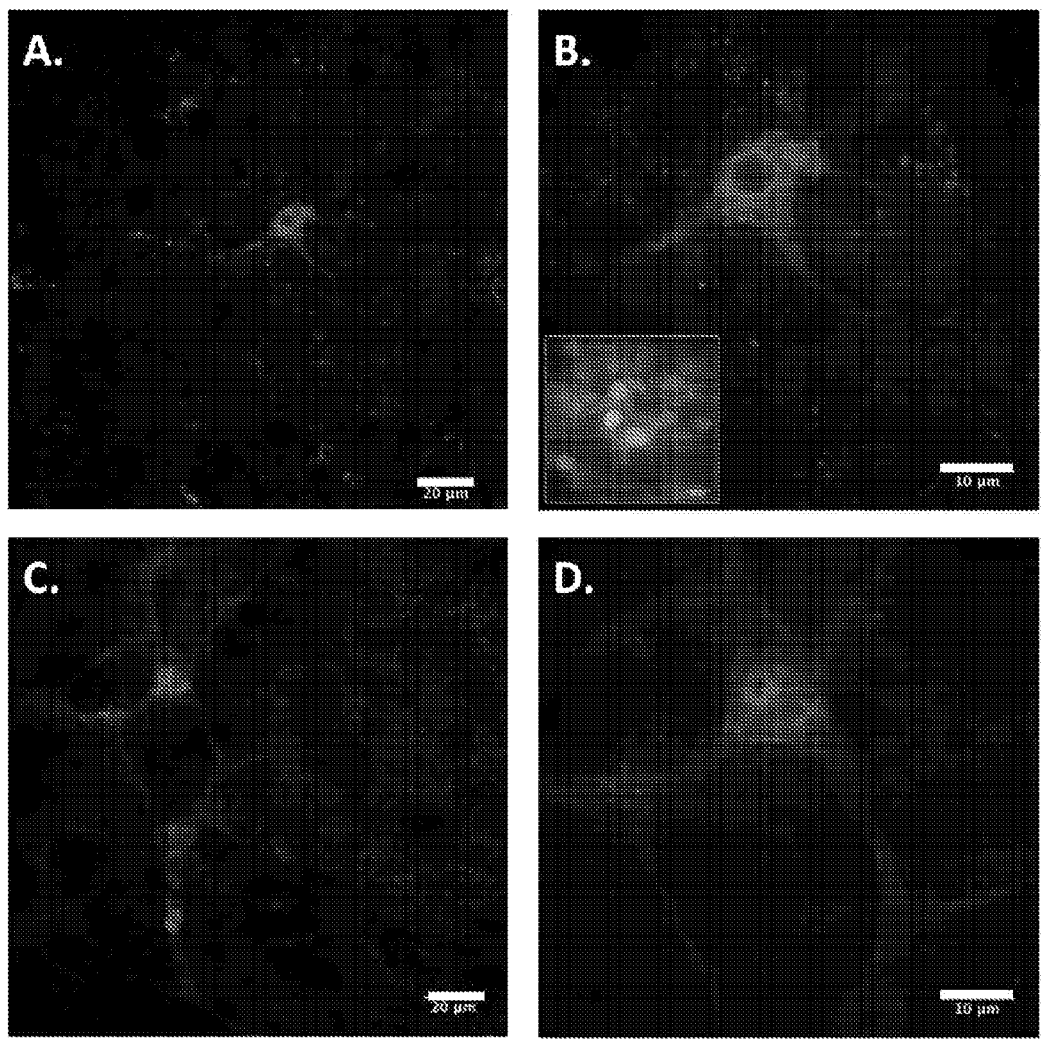
FIGS. 17A through 17D show representative pyramidal neurons showing uptake and diffusion of the CL4 QD-peptide complex into the soma and continuing through the neuronal processes.
Figure 18:
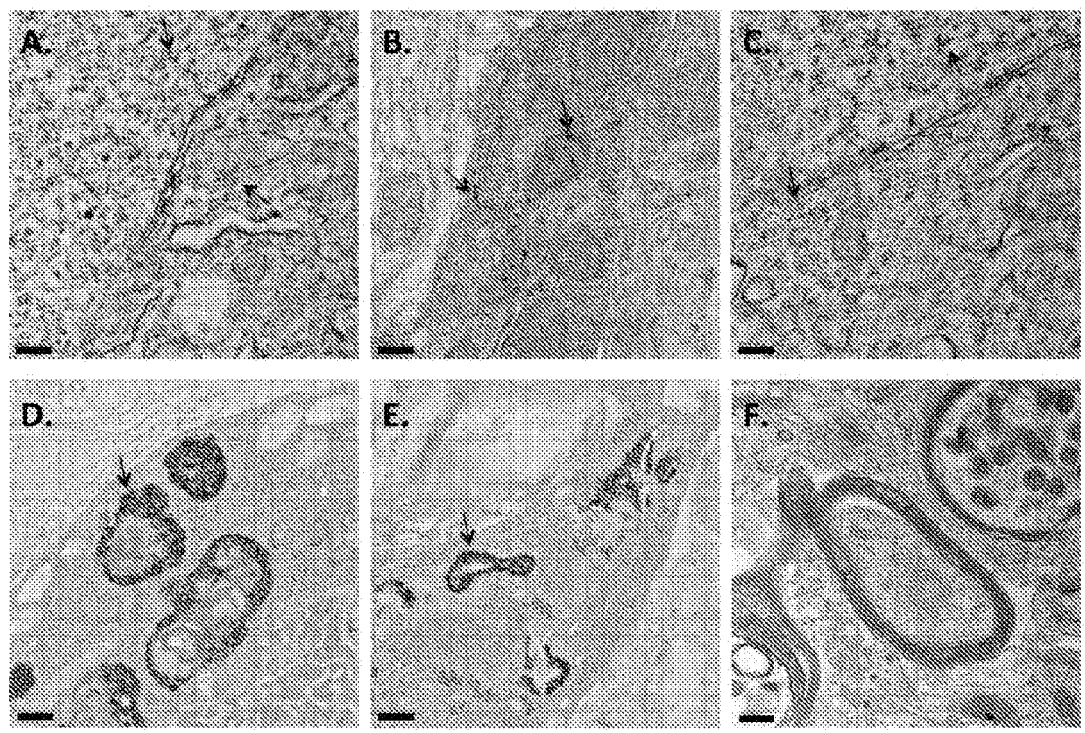
FIGS. 18A through 18F show electron microscopy depicting CL4 QD delivery with or without peptide to the cytosol of hippocampal neurons.

In addition to observing a punctate, perinuclear distribution of QDs in the CA3 cell layer of the hippocampus following application of the CL4 coated QD-peptide complex, pyramidal neurons outside of this region showed a more diffuse distribution of QD-peptide conjugates indicating successful escape from the endolysosomal system and subsequent release into the cytosol that was not restricted to the pyramidal cell body but included the neuronal processes as well (FIG. 17). This diffuse fluorescence was only observed with the CL4 coated QDs conjugated to the Palm1 peptide, and not the CL4 coated QDs alone, suggesting following these data up with electron microscopy. Previous work demonstrated endolysosomal escape with this peptide using only isolated HEK 293T/17 cell cultures (see above and Delehanty, et al. 2010). It is now apparent that this peptide exhibits a similar effect in neurons in a hippocampal slice culture system that contains many non-neuronal cell types that were not affected, thus demonstrating a remarkable specificity for this coat and efficacy for this peptide in a much more complex model system. Electron microscopy confirmed that the CL4 QDs were being transported to the cytosol, were not cytotoxic and were not forming large aggregates when conjugated to Palm1 (FIGS. 18A-18C). However, CL4 QDs without peptide, while still targeting neurons, remained sequestered within intracellular compartments (FIGS. 18D and 18E), validating the fluorescent data.

Concluding Remarks on Neuronal Targeting

The results herein demonstrate that nanoparticles can be selectively targeted to neurons in a structured tissue preparation, thus providing an example of a versatile delivery system that could be used to target drugs to neurons in the mammalian CNS. CL4 QD-Palm1 application showed neuron specific, punctate delivery to the perinuclear region of neuronal cell bodies in the CA3 cell layer of hippocampal slice cultures with no toxicity or morphological changes (up to 72 h in culture). Additionally, pyramidal neurons outside the CA3 cell layer showed robust and diffuse QD uptake in both the soma and their associated processes. Cytosolic delivery, dependent upon the Palm1 peptide, was further visualized through electron microscopy. No intracellular delivery to associated cells was observed across multiple experiments leading to the conclusion that the negatively heterocharged (polyampholyte) nature of the CL4 coating appears to be critical in mediating uptake in a neuronal specific manner since the neutral charged PEG coating did not have this property.

Non-hydrolyzable peptides such as GDap(Pal)VKIKK (Palm1) are competitive inhibitors of Palmitoyl Protein Thioesterase 1 (PPT1) in the low micromolar range (Dawson, et al. 2010). They are taken up readily by cells by virtue of their basic amino acid sequences and function to some extent as chaperones in lymphoblasts from Battens patients with missense mutations which lead to misfolded PPT1 protein and subsequent destruction by the endoplasmic reticulum stress response and ubiquitination (Dawson et al., 2010). It was desired to utilize semiconductor QDs as a fluorescent tag for visualization of Palm1 delivery into the CNS. Unexpectedly, the presence of the palmitate-peptide structure was shown to confer the function of endosomal escape on the peptide when conjugated to a PEG-coated QD in HEK 293 cell culture (see above and Delahanty et al., 2010). The results described herein extends this finding by not only showing that endosomal escape is possible in a much more complex culture system, by utilizing structured tissue in the form of a hippocampal slice culture, but also showing that when the peptide is paired with the CL4 coat, the QD-Palm1 complex specifically targets neurons and then escapes into the cytosol. This neuronal specificity may be attributed to the zwitterionic nature of the CL4 coat since it is not observable with neutrally charged PEG. Further, the peptide appears to remain attached to the QD (by virtue of the binding of the polyhistidine sequence to the Zn in the QD) based on previous FRET studies in cultured cells (Delehanty et al., 2010).

Thus, semiconductor QDs, and presumably other nanoparticles, coated with CL4 can be used to target neurons while avoiding non-neuronal cells with little to no toxicity in a hippocampal slice culture model. Additionally, a sequence derived from the Palm1 peptide, while potentially acting as a chaperone of misfolded PPT1 in Battens patients (Dawson, et al. 2010), can additionally be used as an effector of endosomal escape for the CL4 QDs. Concern over the possible toxicity and biodistribution of CdSe/ZnS core-shell QDs has recently been addressed in Sprague-Dawley rats (Hauck et al., 2012) and rhesus monkeys (Ye et al., 2012) and no appreciable toxicity was observed after several months, even after breakdown of the QDs. Both used 1 mg/kg cadmium and biochemical markers were in the normal range after 90 days, with two treated monkeys showing no ill effects after one year. Together, these findings suggest a neurotherapeutic application for peptide conjugated QDs, which display minimal photobleaching are non-toxic and can deliver biologically active compound, such as drugs, specifically to subcellular compartments of neurons. Thus QD-delivery systems can be an effective therapeutic vehicle for a variety of CNS disorders.

REFERENCES (1) Yun-Pei Chang, Pinaud, F., Antelman, J., Weiss, S. (2008) Tracking bio-molecules in live cells using quantum dots. *Journal of Biophotonics* 1, 287-298.

(2) Juzenas, P., Chen, W., Sun, Y.-P., Coelho, M. A. N., Generalov, R., Generalova, N., and Christensen, I. L. (2008) Quantum dots and nanoparticles for photodynamic and radiation therapies of cancer. *Advanced Drug Delivery Reviews* 60, 1600-1614.

(3) Hild, W. A., Breunig, M., and Goepferich, A. (2008) Quantum dots—Nano-sized probes for the exploration of cellular and intracellular targeting. *European Journal of Pharmaceutics and Biopharmaceutics* 68, 153-168.

(4) Parak, W., Pellegrino, T., and Plank, C. (2005) Labelling of cells with quantum dots. *Nanotechnology* 16, R9-R25.

(5) Alivisatos, A. P., Gu, W., and Larabell, C. A. (2005) Quantum dots as cellular probes. *Ann. Rev. Biomed. Eng.* 7, 55-76.

(6) Jaiswal, J. K., Mattoussi, H., Mauro, J. M., and Simon, S. M. (2003) Long-term multiple color imaging of live cells using quantum dot bioconjugates. *Nat Biotechnol* 21, 47-51.

(7) Alivisatos, P. (2004) The use of nanocrystals in biological detection. *Nature Biotech.* 22, 47-52.

(8) Medintz, I., Uyeda, H., Goldman, E., and Mattoussi, H. (2005) Quantum dot bioconjugates for imaging, labeling and sensing. *Nature Mat.* 435-446.

(9) Parak, W. J., Gerion, D., Pellegrino, T., Zanchet, D., Micheel, C., Williams, S. C., Boudreau, R., Le Gros, M. A., Larabell, C. A., and Alivisatos, A. P. (2003) Biological applications of colloidal nanocrystals. *Nanotech.* 14, R15-R27.

(10) Delehanty, J. B., Mattoussi, H., and Medintz, I. L. (2009) Delivering quantum dots into cells: strategies, progress and remaining issues. *Anal Bioanal Chem* 393, 1091-105.

(11) Payne, C. K., Jones, S. A., Chen, C., and Zhuang, X. (2007) Internalization and trafficking of cell surface proteoglycans and proteoglycan-binding ligands. *Traffic* 8, 389-401.

(12) Ruan, G., Agrawal, A., Marcus, A. I., and Nie, S. (2007) Imaging and tracking of tat peptide-conjugated quantum dots in living cells: new insights into nanoparticle uptake, intracellular transport, and vesicle shedding. *J Am Chem Soc* 129, 14759-66.

(13) Delehanty, J. B., Medintz, I. L., Pons, T., Brunel, F. M., Dawson, P. E., and Mattoussi, H. (2006) Self-assembled quantum dot-peptide bioconjugates for selective intracellular delivery. *Bioconjug Chem* 17, 920-7.

(14) Sapsford, K. E., Pons, T., Medintz, I. L., Higashiya, S., Brunel, F. M., Dawson, P. E., and Mattoussi, H. (2007) Kinetics of metal-affinity driven self-assembly between proteins or peptides and CdSe—ZnS quantum dots. *J. Phys. Chem. C* 111, 11528-11538.

(15) Vivès, E., Schmidt, J., and Pèlegrin, A. (2008) Cell-penetrating and cell-targeting peptides in drug delivery. *Biochimica et Biophysica Acta (BBA)-Reviews on Cancer* 1786, 126-138.

(16) Medintz, I. L., Pons, T., Delehanty, J. B., Susumu, K., Brunel, F. M., Dawson, P. E., and Mattoussi, H. (2008) Intracellular Delivery of Quantum Dot-Protein Cargos Mediated by Cell Penetrating Peptides. *Bioconjug Chem.*

(17) Mattoussi, H., Mauro, J. M., Goldman, E. R., Anderson, G. P., Sundar, V. C., Mikulec, F. V., and Bawendi, M. G. (2000) Self-Assembly of CdSe—ZnS Quantum Dot Bioconjugates Using an Engineered Recombinant Protein. *J. Am. Chem. Soc.* 122, 12142-12150.

(18) Mei, B. C., Susumu, K., Medintz, I. L., Delehanty, J. B., Mountziaris, T. J., and Mattoussi, H. (2008) Modular poly(ethylene glycol) ligands for biocompatible semiconductor and gold nanocrystals with extended pH and ionic stability. *J. Mat. Chem.* 18, 1-11.

(19) Schnolzer, M., Alewood, P., Jones, A., Alewood, D., and Kent, S. B. (1992) In situ neutralization in Boc-chemistry solid phase peptide synthesis. Rapid, high yield assembly of difficult sequences. *Int. J. Pept. Protein. Res.* 40, 180-93.

(20) Marchenko, S., and Flanagan, L. (2007) Transfecting human neural stem cells with the Amaxa Nucleofector. *J Vis Exp,* 240.

(21) Iversen, N., Birkenes, B., Torsdalen, K., and Djurovic, S. (2005) Electroporation by nucleofector is the best nonviral transfection technique in human endothelial and smooth muscle cells. *Genet Vaccines Ther* 3, 2.

(22) Quintana, A., and Hoth, M. (2004) Apparent cytosolic calcium gradients in T-lymphocytes due to fura-2 accumulation in mitochondria. *Cell Calcium* 36, 99-109.

(23) Clapp, A. R., Pons, T., Medintz, I. L., Delehanty, J. B., Melinger, J. S., Tiefenbrunn, T., Dawson, P. E., Fisher, B. R., O'Rourke, B., and Mattoussi, H. (2007) Two-photon excitation of quantum dot-based fluorescence resonance energy transfer and its applications. *Advanced Materials* 119, 1921-1926.

(24) Mosmann, T. (1983) Rapid colorimetric assay for cellular growth and survival: application to proliferation and cytotoxicity assays. *J Immunol Methods* 65, 55-63.

(25) Tekle, C., Deurs, B., Sandvig, K., and Iversen, T. G. (2008) Cellular trafficking of quantum dot-ligand bioconjugates and their induction of changes in normal routing of unconjugated ligands. *Nano Lett* 8, 1858-65.

(26) Bharali, D. J., Lucey, D. W., Jayakumar, H., Pudavar, H. E., and Prasad, P. N. (2005) Folate-receptor-mediated delivery of InP quantum dots for bioimaging using confocal and two-photon microscopy. *J Am Chem Soc* 127, 11364-71.

(27) Qian, J., Yong, K. T., Roy, I., Ohulchanskyy, T. Y., Bergey, E. J., Lee, H. H., Tramposch, K. M., He, S., Maitra, A., and Prasad, P. N. (2007) Imaging pancreatic cancer using surface-functionalized quantum dots. *J Phys Chem B* 111, 6969-72.

(28) Kornfeld, S., and Mellman, I. (1989) The biogenesis of lysosomes. *Annu Rev Cell Biol* 5, 483-525.

(29) Honey, K., and Rudensky, A. Y. (2003) Lysosomal cysteine proteases regulate antigen presentation. *Nat Rev Immunol* 3, 472-82.

(30) Neumann, E., Schaefer-Ridder, M., Wang, Y., and Hofschneider, P. H. (1982) Gene transfer into mouse lyoma cells by electroporation in high electric fields. *Embo J* 1, 841-5.

(31) Derfus, A. M., Chan, W. C. W., and Bhatia, S. N. (2004) Intracellular delivery of quantum dots for live cell labeling and organelle tracking. *Advanced Materials* 16, 961-+.

(32) Chen, F. Q., and Gerion, D. (2004) Fluorescent CdSe/ZnS nanocrystal-peptide conjugates for long-term, non-toxic imaging and nuclear targeting in living cells. *Nano Letters* 4, 1827-1832.

(33) Conner, S. D., and Schmid, S. L. (2003) Regulated portals of entry into the cell. *Nature* 422, 37-44.

(34) Nichols, B. J., and Lippincott-Schwartz, J. (2001) Endocytosis without clathrin coats. *Trends Cell Biol* 11, 406-12.

(35) Neu, M., Fischer, D., and Kissel, T. (2005) Recent advances in rational gene transfer vector design based on poly(ethylene imine) and its derivatives. *J Gene Med* 7, 992-1009.

(36) Hoekstra, D., Rejman, J., Wasungu, L., Shi, F., and Zuhorn, I. (2007) Gene delivery by cationic lipids: in and out of an endosome. *Biochem Soc Trans* 35, 68-71.

(37) Uyeda, H. T., Medintz, I. L., Jaiswal, J. K., Simon, S. M., and Mattoussi, H. (2005) Synthesis of compact multidentate ligands to prepare stable hydrophilic quantum dot fluorophores. *J Am Chem Soc* 127, 3870-8.

(38) Duan, H., and Nie, S. (2007) Cell-penetrating quantum dots based on multivalent and endosome-disrupting surface coatings. *J Am Chem Soc* 129, 3333-8.

(39) Jablonski, A. E., Humphries, W. H., and Payne, C. K. (2009) Pyrenebutyrate-mediated delivery of quantum dots across the plasma membrane of living cells. *J Phys Chem B* 113, 405-8.

(40) El-Andaloussi, S., Holm, T., and Langel, U. (2005) Cell-penetrating peptides: Mechanisms and applications. *Current Pharmaceutical Design* 11, 3597-3611.

(41) Melikov, K., and Chemomordik, L. V. (2005) Arginine-rich cell penetrating peptides: from endosomal uptake to nuclear delivery. *Cell Mol Life Sci* 62, 2739-49.

(42) Zhao, M., and Weissleder, R. (2004) Intracellular cargo delivery using tat peptide and derivatives. *Med Res Rev* 24, 1-12.

(43) Abes, S., Williams, D., Prevot, P., Thierry, A., Gait, M. J., and Lebleu, B. (2006) Endosome trapping limits the efficiency of splicing correction by PNA-oligolysine conjugates. *J Control Release* 110, 595-604.

(44) Kato, T., Okada, S., Yutaka, T., and Yabuuchi, H. (1984) The effects of sucrose loading on lysosomal hydrolases. *Mol Cell Biochem* 60, 83-98.

(45) Ferrari, V., and Cutler, D. J. (1991) Kinetics and thermodynamics of chloroquine and hydroxychloroquine transport across the human erythrocyte membrane. *Biochem Pharmacol* 41, 23-30.

(46) Rozenzhak, S. M., Kadakia, M. P., Caserta, T. M., Westbrook, T. R., Stone, M. O., and Naik, R. R. (2005) Cellular internalization and targeting of semiconductor quantum dots. *Chemical Communications*, 2217-2219.

(47) Cho, S., Dawson, P. E., and Dawson, G. (2000) Antisense palmitoyl protein thioesterase 1 (PPT1) treatment inhibits PPT1 activity and increases cell death in LA-N-5 neuroblastoma cells. *J Neurosci Res* 62, 234-40.

(48) Dawson, G., Dawson, S. A., Marinzi, C., and Dawson, P. E. (2002) Anti-tumor promoting effects of palmitoyl: protein thioesterase inhibitors against a human neurotumor cell line. *Cancer Lett* 187, 163-8.

(49) Rabanal, F., Ludevid, M. D., Pons, M., and Giralt, E. (1993) CD of proline-rich polypeptides: application to the study of the repetitive domain of maize glutelin-2. *Biopolymers* 33, 1019-28.

(50) Pujals, S., and Giralt, E. (2008) Proline-rich, amphipathic cell-penetrating peptides. *Adv Drug Deliv Rev* 60, 473-84.

(51) Fernandez-Carneado, J., Kogan, M. J., Van Mau, N., Pujals, S., Lopez-Iglesias, C., Heitz, F., and Giralt, E. (2005) Fatty acyl moieties: improving Pro-rich peptide uptake inside HeLa cells. *J Pept Res* 65, 580-90.

(52) Daniels, D. S., and Schepartz, A. (2007) Intrinsically cell-permeable miniature proteins based on a minimal cationic PPII motif. *J Am Chem Soc* 129, 14578-9.

(53) del Pozo-Rodriguez, A., Pujals, S., Delgado, D., Solinis, M. A., Gascon, A. R., Giralt, E., and Pedraz, J. L. (2009) A proline-rich peptide improves cell transfection of solid lipid nanoparticle-based non-viral vectors. *J Control Release* 133, 52-9.

(54) Pujals, S., Bastus, N. G., Pereiro, E., Lopez-Iglesias, C., Puntes, V. F., Kogan, M. J., and Giralt, E. (2009) Shuttling gold nanoparticles into tumoral cells with an amphipathic proline-rich peptide. *Chembiochem* 10, 1025-31.

(55) McGrath, J. P., Capon, D. J., Smith, D. H., Chen, E. Y., Seeburg, P. H., Goeddel, D. V., and Levinson, A. D. (1983) Structure and organization of the human Ki-ras proto-oncogene and a related processed pseudogene. *Nature* 304, 501-6.

(56) Resh, M. D. (1996) Regulation of cellular signalling by fatty acid acylation and prenylation of signal transduction proteins. *Cell Signal* 8, 403-12.

(57) Resh, M. D. (1999) Fatty acylation of proteins: new insights into membrane targeting of myristoylated and palmitoylated proteins. *Biochim Biophys Acta* 1451, 1-16.

(58) Dunphy, J. T., and Linder, M. E. (1998) Signalling functions of protein palmitoylation. *Biochim Biophys Acta* 1436, 245-61.

(59) Medintz, I. L., Clapp, A. R., Brunel, F. M., Tiefenbrunn, T., Uyeda, H. T., Chang, E. L., Deschamps, J. R., Dawson, P. E., and Mattoussi, H. (2006) Proteolytic activity monitored by fluorescence resonance energy transfer through quantum-dot-peptide conjugates. *Nature Materials* 5, 581-589.

(60) Boeneman, K., Mei, B. C., Dennis, A. M., Bao, G., Deschamps, J. R., Mattoussi, H., and Medintz, I. L. (2009) Sensing caspase 3 activity with quantum dot-fluorescent protein assemblies. *J Am Chem Soc* 131, 3828-9.

(61) Pons, T., Uyeda, H. T., Medintz, I. L., and Mattoussi, H. (2006) Hydrodynamic Dimensions, Electrophoretic Mobility, and Stability of Hydrophilic Quantum Dots. *The Journal of Physical Chemistry B* 110, 20308-20316.

ADDITIONAL REFERENCES

Algar, W. R., Susumu, K., Delehanty, J. B., and Medintz, I. L. (2011), Semiconductor Quantum Dots in Bioanalysis: Crossing the Valley of Death, Anal Chem, 83, 8826-8837.

Arakawa, T., Ejima, D., Kita, Y., and Tsumoto, K. (2006), Small Molecule Pharmacological Chaperones: From Thermodynamic Stabilization to Pharmaceutical Drugs, Biochim Biophys Acta, 1764, 1677-1687.

Courel, M. N., Girard, N., Delpech, B., and Chauzy, C. (1986), Specific Monoclonal Antibodies to Glial Fibrillary Acidic Protein (Gfap), J Neuroimmunol, 11, 271-276.

Dawson, G., Schroeder, C., and Dawson, P. E. (2010), Palmitoyl:Protein Thioesterase (Pptl) Inhibitors Can Act as Pharmacological Chaperones in Infantile Batten Disease, Biochem Biophys Res Commun, 395, 66-69.

Delehanty, J. B., et al. (2010), Delivering Quantum Dot-Peptide Bioconjugates to the Cellular Cytosol: Escaping from the Endolysosomal System, Integr Biol (Camb), 2, 265-277.

Delehanty, J. B., Mattoussi, H., and Medintz, I. L. (2009), Delivering Quantum Dots into Cells: Strategies, Progress and Remaining Issues, Anal Bioanal Chem, 393, 1091-1105.

Delehanty, J. B., et al. (2006), Self-Assembled Quantum Dot-Peptide Bioconjugates for Selective Intracellular Delivery, Bioconjug Chem, 17, 920-927.

Emerich, D. F., and Thanos, C. G. (2006), The Pinpoint Promise of Nanoparticle-Based Drug Delivery and Molecular Diagnosis, Biomolecular Engineering, 23, 171-184.

Fan, J. Q., and Ishii, S. (2007), Active-Site-Specific Chaperone Therapy for Fabry Disease. Yin and Yang of Enzyme Inhibitors, FEBS J, 274, 4962-4971.

Grinberg, Y. Y., Milton, J. G., and Kraig, R. P. (2011), Spreading Depression Sends Microglia on Levy Flights, PLoS One, 6, e19294.

Grinberg, Y. Y., van Drongelen, W., and Kraig, R. P. (2012), Insulin-Like Growth Factor-1 Lowers Spreading Depression Susceptibility and Reduces Oxidative Stress, J Neurochem.

Hild, W. A., Breunig, M., and Goepferich, A. (2008), Quantum Dots—Nano-Sized Probes for the Exploration of Cellular and Intracellular Targeting, European Journal of Pharmaceutics and Biopharmaceutics, 68, 153-168.

Hulse, R. E., Kunkler, P. E., Fedynyshyn, J. P., and Kraig, R. P. (2004), Optimization of Multiplexed Bead-Based Cytokine Immunoassays for Rat Serum and Brain Tissue, J Neurosci Methods, 136, 87-98.

Kunkler, P. E., Hulse, R. E., Schmitt, M. W., Nicholson, C., and Kraig, R. P. (2005), Optical Current Source Density Analysis in Hippocampal Organotypic Culture Shows That Spreading Depression Occurs with Uniquely Reversing Currents, J Neurosci, 25, 3952-3961.

Kunkler, P. E., and Kraig, R. P. (1997), Reactive Astrocytosis from Excitotoxic Injury in Hippocampal Organ Culture Parallels That Seen in Vivo, J Cereb Blood Flow Metab, 17, 26-43.

Kunkler, P. E., and Kraig, R. P. (1998), Calcium Waves Precede Electrophysiological Changes of Spreading Depression in Hippocampal Organ Cultures, The Journal of Neuroscience, 18, 3416-3425.

Kunkler, P. E., and Kraig, R. P. (2004), PLO Ca2+ Channel Blockade Stops Spreading Depression and Related Pyramidal Neuronal Ca2+ Rise in Hippocampal Organ Culture, Hippocampus, 14, 356-367.

Mei, B. C., et al. (2008), Modular Poly(Ethylene Glycol) Ligands for Biocompatible Semiconductor and Gold Nanocrystals with Extended Ph and Ionic Stability, Journal of Materials Chemistry, 18, 4949-4958.

Mihrimah, O. (2004), Quantum Dots and Other Nanoparticles: What Can They Offer to Drug Discovery?, Drug Discovery Today, 9, 1065-1071.

Minami, S. S., et al. (2012), Selective Targeting of Microglia by Quantum Dots, J Neuroinflammation, 9, 22.

Mitchell, H. M., White, D. M., and Kraig, R. P. (2010), Strategies for Study of Neuroprotection from Cold-Preconditioning, J Vis Exp, e2192.

Parenti, G. (2009), Treating Lysosomal Storage Diseases with Pharmacological Chaperones: From Concept to Clinics, EMBO Mol Med, 1, 268-279.

Prapainop, K., Witter, D. P., and Wentworth, P. (2012), A Chemical Approach for Cell-Specific Targeting of Nanomaterials, Small Molecule-Initiated Misfolding of Nanoparticle Corona Proteins, J Am Chem Soc.

Pusic, A. D., Grinberg, Y. Y., Mitchell, H. M., and Kraig, R. P. (2011), Modeling Neural Immune Signaling of Episodic and Chronic Migraine Using Spreading Depression in Vitro, J Vis Exp.

Quinn, B., Toga, A. W., Motamed, S., and Merlic, C. A. (1995), Fluoro Nissl Green: A Novel Fluorescent Counterstain for Neuroanatomy, Neurosci Lett, 184, 169-172.

Rehberg, M., et al. (2010), Quantum Dots Modulate Leukocyte Adhesion and Transmigration Depending on Their Surface Modification, Nano Lett, 10, 3656-3664.

Ruan, Y., Yao, L., Zhang, B., Zhang, S., and Guo, J. (2012), Nanoparticle-Mediated Delivery of Neurotoxin-Ii to the Brain with Intranasal Administration: An Effective Strategy to Improve Antinociceptive Activity of Neurotoxin, Drug Dev Ind Pharm, 38, 123-128.
Sapsford, K. E., et al. (2007), Kinetics of Metal-Affinity Driven Self-Assembly between Proteins or Peptides and Cdse—Zns Quantum Dots, The Journal of Physical Chemistry C, 111, 11528-11538.
Smith, B. R., et al. (2008), Real-Time Intravital Imaging of Rgd-Quantum Dot Binding to Luminal Endothelium in Mouse Tumor Neovasculature, Nano Lett, 8, 2599-2606.
Streit, W. J. (1990), An Improved Staining Method for Rat Microglial Cells Using the Lectin from *Griffonia Simplicifolia* (Gsa I-B4), J Histochem Cytochem, 38, 1683-1686.
Susumu, K., et al. (2011), Multifunctional Compact Zwitterionic Ligands for Preparing Robust Biocompatible Semiconductor Quantum Dots and Gold Nanoparticles, J Am Chem Soc, 133, 9480-9496.
Susumu, K., et al. (2007), Enhancing the Stability and Biological Functionalities of Quantum Dots Via Compact Multifunctional Ligands, J Am Chem Soc, 129, 13987-13996.
Watanabe, M., et al. (2006), Monoclonal Antibody Rip Specifically Recognizes 2',3'-Cyclic Nucleotide 3'-Phosphodiesterase in Oligodendrocytes, J Neurosci Res, 84, 525-533.

What is claimed is:

1. A method of delivery of a nanoparticle to a neuron in a tissue, the method comprising:

providing to the tissue a nanoparticle bound to a compound of the formula:

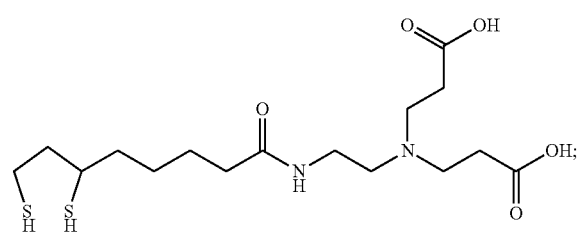 [SMILES: O=C(O)CCN(CCNC(=O)CCCCC(S)CCS)CCC(=O)O]

and subsequently detecting the nanoparticles in neurons in the tissue.

2. The method of claim 1, wherein the nanoparticle is also bound to a peptide comprising (a) a nanoparticle association domain, (b) a spacer domain, (c) an uptake domain, and (d) a vesicle escape domain comprising a non-hydrolyzable lipid moiety, wherein the spacer domain is between the nanoparticle association domain and the uptake and vesicle escape domains.

3. The method of claim 2, wherein the peptide comprises Palm-1.

4. The method of claim 1, wherein the nanoparticle is a quantum dot.

5. The method of claim 1, wherein the compound bound to the nanoparticle is effective to induce preferential uptake of the nanoparticle by neuronal cells.

6. The method of claim 1, wherein the nanoparticle is also bound to a drug.

7. The method of claim 1, wherein the tissue is in a living organism.

8. A method of labeling a neuron in a tissue, the method comprising:

provinding to the tissue providing to the tissue a nanoparticle bound to:

(1) a compound of the formula:

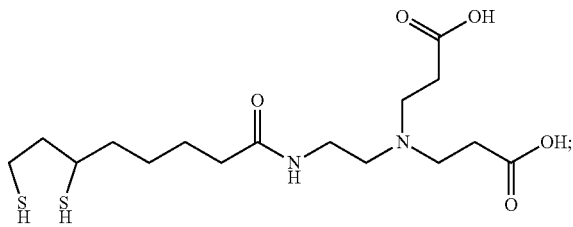 [SMILES: O=C(O)CCN(CCNC(=O)CCCCC(S)CCS)CCC(=O)O]

and (2) peptide comprising
  (a) a nanoparticle association domain comprising polyhistidine;
  (b) a spacer domain comprising 8, 9, or 10 proline residues;
  (c) an uptake domain comprising SEQ ID No: 7; and
  (d) a vesicle escape domain comprising a non-hydrolyzable palmitic acid,
  wherein the spacer domain is between the nanoparticle association domain and the uptake and vesicle escape domains; and subsequently detecting the nanoparticles in the neuron.

9. The method of claim 8, wherein the non-hydrolyzable palmitic acid is palmitoyldiamoniproprionyl.

10. The method of claim 8, wherein the spacer domain comprises 9 proline residues.

11. The method of claim 8, wherein the peptide comprises SEQ ID No: 3 or SEQ ID No: 4.

12. The method of claim 8, wherein the nanoparticle is also bound to a drug.

13. The method of claim 8, wherein the tissue is in a living organism.

* * * * *